United States Patent
Norris et al.

(10) Patent No.: US 6,346,624 B1
(45) Date of Patent: Feb. 12, 2002

(54) PROCESS FOR MAKING 5-LIPOXYGENASE INHIBITORS HAVING VARIED HETEROCYCLIC RING SYSTEMS

(75) Inventors: Timothy Norris, Gales Ferry, CT (US); Megan E. Hnatow, Charlestown, MA (US); John F. Lambert, North Stonington, CT (US)

(73) Assignee: Pfizer Inc, New York, NY (US)

( * ) Notice: Subject to any disclaimer, the term of this patent is extended or adjusted under 35 U.S.C. 154(b) by 3 days.

(21) Appl. No.: 09/607,011

(22) Filed: Jun. 29, 2000

Related U.S. Application Data
(60) Provisional application No. 60/151,615, filed on Aug. 31, 1999.

(51) Int. Cl.[7] .............................................. C07D 233/60
(52) U.S. Cl. .................................................... 548/311.1
(58) Field of Search ...................................... 548/311.1

(56) References Cited

U.S. PATENT DOCUMENTS

| | | | | |
|---|---|---|---|---|
| 5,883,106 A | * | 3/1999 | Stevens et al. | 514/277 |
| 6,063,928 A | * | 5/2000 | Stevens et al. | 546/269.7 |
| 6,239,285 B1 | * | 5/2001 | Norris et al. | 548/304.7 |

FOREIGN PATENT DOCUMENTS

WO  9611911  4/1996

OTHER PUBLICATIONS

Migita, et al., *Bull. Chem. Soc. Japan*, vol. 53, pp. 1385–1389 (1980).
Takagi, *Chemistry Letters*, pp. 2221–2224 (1987).
Brocato, et al., *Tetrahedron Lett.*, vol. 33, pp. 7433–7436 (1992).
Arcadi, et al., *Tetraahedron Lett.*, vol. 34, pp. 2813–2816 (1993).
McClure, et al., *J. Amer. Chem. Soc.*, vol. 115, pp. 6094–6100 (1993).
Nuss, et al., *J. Am. Chem. Soc.*, vol. 115, pp. 6691–6692 (1993).
Paquette, et al.,*J. Org. Chem.*, vol. 58, pp. 165–169 (1993).

* cited by examiner

*Primary Examiner*—Floyd D. Higel
*Assistant Examiner*—Andrea DiSouza Small
(74) *Attorney, Agent, or Firm*—Peter C. Richardson; Paul H. Ginsburg; Raymond M. Speer

(57) ABSTRACT

A novel process intermediate, tetrahydro-4-[3-(4-fluorophenyl)thio]phenyl-2H-pyran-4-carboxamide, of the formula:

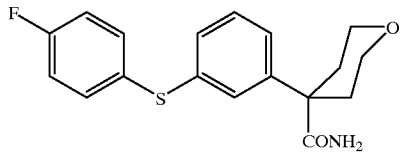

is described, as well as its use in a process of preparing 5-lipoxygenase inhibitors of the formula:

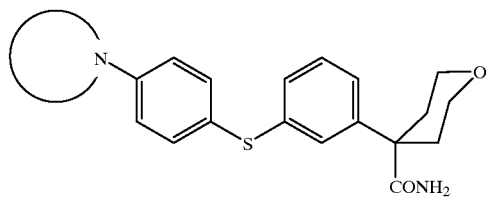

which comprises establishing a reaction mixture consisting of:

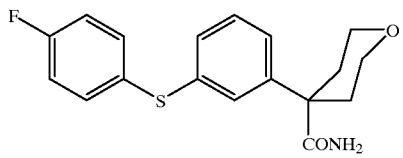

and
an electron deficient monocyclic or benzo-fused bicyclic N-heterocycle containing two nitrogen atoms of the formula:

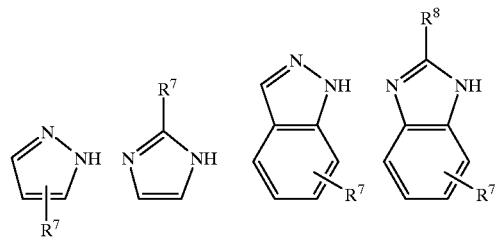

in an aprotic solvent; in the presence of a carbonate of the formula: $(M)_2$-$CO_3$, where M is an alkali metal, Group 1/Ia element, selected from the group consisting of lithium, Li; sodium,Na; potassium, K; rubidium, Rb; and cesium, Cs; followed by heating of said reaction mixture under a nitrogen atmosphere; whereby there is produced the desired compound of the above-recited formula.

2 Claims, No Drawings

PROCESS FOR MAKING 5-LIPOXYGENASE INHIBITORS HAVING VARIED HETEROCYCLIC RING SYSTEMS

This appln claims benefit of Prov. No. 60/151,615 filed Aug. 31, 1999.

REFERENCE TO COPENDING APPLICATIONS

Reference is made to application Ser. No. 09/207,342 filed Dec. 8, 1998; which is a divisional of application Ser. No. 09/020,014 filed Feb. 6, 1998, now U.S. Pat. No. 5,883,106; which is a continuation of application Ser. No. 08/809,901 filed May 29, 1995, now abandoned; claiming priority from application Ser. No. PCT/JP94/01747 filed Oct. 18, 1994, now abandoned; and a §371 of application Ser. No. PCT/IB95/00408 filed May 29, 1995, now lapsed, and published as WO 96/11911 on Apr. 25, 1996, which discloses 5-lipoxygenase inhibitors useful in the treatment of inflammatory diseases and allergy. Several processes for preparing said 5-lipoxygenase inhibitors are described therein, but nothing that is disclosed would teach the person of ordinary skill the improved process of the present invention.

Reference is also made to copending application Ser. No. 60/113,221 filed Dec. 22, 1998, which discloses a novel process for preparing 4-{3-[4-(2-methyl-imidazol-1-yl)-phenyl sulfanyl]-phenyl}-tetrahydro-pyran-4-carboxylic acid amide methyl sulfonate. However, said disclosed process is not the same as that of the present invention.

Reference is further made to copending applications filed of even date with the instant application, Ser. Nos. 09/606,609 and 09/606,318 which also involve processes of making 5-lipoxygenase inhibitors having varied heterocyclic ring systems and which have some process elements in common with the process of the instant application.

BACKGROUND OF THE INVENTION

There is disclosed in WO 96/11911 a class of novel compounds active as inhibitors of the activity of the 5-lipoxygenase enzyme, characterized by the following structural Formula (1.1.0):

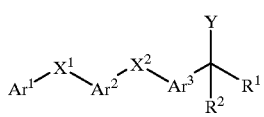

(1.1.0)

wherein:
- $Ar^1$ is a heterocyclic moiety selected from the group consisting of imidazolyl; pyrrolyl; pyrazolyl; 1,2,3-triazolyl; 1,2,4-triazolyl; indolyl; indazolyl; and benzimidazolyl; bonded to $X^1$ through a ring nitrogen atom; and substituted with 0–2 substituents selected from the group consisting of halo; hydroxy; cyano; amino; $(C_1–C_4)$ alkyl; $(C_1–C_4)$ alkoxy; $(C_1–C_4)$ alkylthio; $(C_1–C_4)$ halo-substituted alkyl; $(C_1–C_4)$ halo-substituted alkoxy; $(C_1–C_4)$ alkylamino; and di$(C_1–C_4)$ alkylamino;
- $X^1$ is a direct bond or $(C_1–C_4)$ alkylene;
- $Ar^2$ is phenylene substituted with 0–2 substituents selected from the group consisting of halo; hydroxy; cyano; amino; $(C_1–C_4)$ alkyl; $(C_1–C_4)$ alkoxy; $(C_1–C_4)$ alkylthio; $(C_1–C_4)$ halo-substituted alkyl; and $(C_1–C_4)$ halo-substituted alkoxy;
- $X^2$ is —A—X— or —X—A— wherein A is a direct bond or $(C_1–C_4)$ alkylene and X is oxy; thio; sulfinyl; or sulfonyl;
- $Ar^3$ is a member selected from the group consisting of phenylene; pyridylene; thienylene; furylene; oxazolylene; and thiazolylene; substituted with 0–2 substituents selected from halo; hydroxy; cyano; amino; $(C_1–C_4)$ alkyl; $(C_1–C_4)$ alkoxy; $(C_1–C_4)$ alkylthio; $(C_1–C_4)$ halo-substituted alkyl; $(C_1–C_4)$ halo-substituted alkoxy; $(C_1–C_4)$ alkylamino; and di$(C_1–C_4)$ alkylamino;
- $R^1$ and $R^2$ are each $(C_1–C_4)$ alkyl; or together they form a group of formula: —$D^1$—Z—$D^2$— which together with the carbon atom to which it is attached defines a ring having 3 to 8 atoms, wherein $D^1$ and $D^2$ are $(C_1–C_4)$ alkylene and Z is a direct bond or oxy; thio; sulfinyl; sulfonyl; or vinylene; and $D^1$ and $D^2$ may be substituted by $(C_1–C_3)$ alkyl; and
- Y is $CONR^3R^4$; CN; $C(R^3)=N—OR^4$; $COOR^3$; $COR^3$; or $CSNR^3R^4$; wherein
- $R^3$ and $R^4$ are each H or $(C_1–C_4)$ alkyl.

With respect to the above-recited compounds, the preferred meaning for $(C_1–C_4)$ halo-substituted alkyl is trifluoromethyl; and the preferred meaning for $(C_1–C_4)$ halo-substituted alkoxy is trifluoromethoxy. A preferred group of the above-recited compounds consists of those wherein $Ar^2$ is 1,4-phenylene and $Ar^3$ is 1,3-phenylene or 5-fluoro-1,3-phenylene. Within said preferred group, more preferred compounds are those in which $Ar^1$ is 2-alkylimidazolyl; $X^1$ is a direct bond; and Y is $CONH_2$; and those in which $Ar^1$ is pyrrolyl; $X^1$ is $CH_2$; and Y is $CONH_2$.

A particularly preferred embodiment of the above-described class of inhibitory compounds is the following compound of Formula (1.0.0):

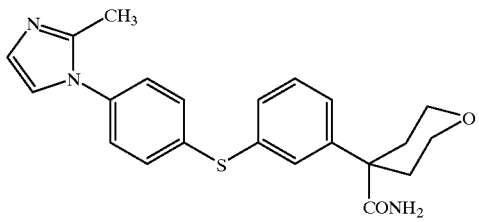

(1.0.0)

Compounds which inhibit the action of lipoxygenase enzyme are useful in the treatment or alleviation of inflammatory diseases, allergy and cardiovascular diseases in mammals including humans. Lipoxygenase enzyme activity occurs as part of the arachidonic acid cascade. Arachidonic acid is the biological precursor of several groups of biologically active endogenous metabolites. Arachidonic acid is first released from membrane phospholipids via the action of phospholipase A2. Arachidonic acid is then metabolized (i) by cyclooxygenase to give prostaglandins including prostacyclin, and thromboxanes; or (ii) by lipoxygenase to give hydroperoxy fatty acids, which may be further converted to leukotrienes.

Leukotrienes, in turn, are extremely potent and elicit a wide variety of biological effects, e.g., peptidoleukotrienes, $LTC_4$, $LTD_4$, and $LTE_4$, are important bronchoconstrictors and vaso-constrictors, and cause plasma extravasation by increasing capillary permeability. $LTB_4$ is a potent chemotactic agent which intensifies leukocyte infiltration and degranulation at a site of inflammation. Leukotrienes have been implicated in a number of human disease states including asthma, chronic obstructive pulmonary disease, allergic rhinitis, rheumatoid arthritis, gout, psoriasis, atopic dermatitis, adult respiratory distress syndrome (ARDS), and inflammatory bowel diseases including. Crohn's disease. An agent which actively inhibits lipoxygenases, and as a consequence the production of leukotrienes, will be of significant therapeutic value in treating acute and chronic inflammatory conditions. See Masamune and Melvin, *Annual Reports in Medicinal Chemistry* 24, 71–80 (1989). Particular lipoxygenase inhibitors have been disclosed in EP 0 462 830; EP 0 505 122; and EP 0 540 165.

Several preparation processes for the lipoxygenase inhibitors described in above-mentioned published application WO 96/39408 are set forth therein. An example of such a preparation process is the coupling of a compound of Formula (1.2.0) and a compound of Formula (1.2.1), which may be represented by the reaction scheme set out below:

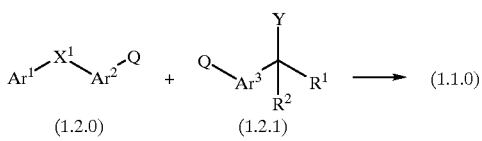

where $X^1$ is thio, and Q is a displaceable group in the presence of thiourea and a suitable catalyst, e.g., tetrakis (triphenylphosphine)-palladium. Reference is made to *Chem. Lett.*, 1379–1380 (1986). Suitable displaceable groups Q are said to include a halo or sulfonyloxy group.

DESCRIPTION OF THE STATE OF THE ART

The present invention is in the field of methods used for synthetic preparation of compounds of the type of Formula (1.0.0), some of which are known compounds, some of which are novel compounds, and some of which are not in the public domain because they cannot be obtained using methods of preparation heretofore known in the art. All of the compounds, however, possess biological activity as inhibitors of 5-lipoxygenase.

As already noted above, it is known in the art that compounds of the type in Formula (1.0.0) may be prepared by a process which initially uses a palladium catalyzed nucleophilic substitution of aryl halides by thiolate anions. Further details of said initial stage of such a process may be found in Migita et al., *Bull. Chem. Soc. Japan* 53, 1385–1389 (1980). Said initial stage may be represented by the following reaction scheme:

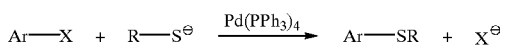

where X is I or Br; and R is phenyl or $(C_1-C_4)$ alkyl.

The technical literature contains a number of disclosures relating to palladium-catalyzed synthesis. See, e.g., Brocato et al., *Tetrahedron Lett.* 33, 7433 (1992), which describes ring formation based on the palladium-, especially $Pd(PPh_3)_4$,-catalyzed reaction of bifunctional aromatic compounds with terminal alkynes and carbon monoxide, requiring both palladium(0) and palladium(II) catalysts.

Arcadi et al., *Tetrahedron Lett.* 34, 2813 (1993) discloses synthesis of 2,3,5-trisubstituted furans from aryl halides and 2-propargyl-1,3-dicarbonyl compounds in the presence of tetrakis(triphenylphosphine)palladium(0) and $K_2CO_3$. It is observed that the nature of the base strongly affects the reaction course.

McClure and Danishefsky, *J. Am. Chem. Soc.* 115, 6094–6100 (1993) discloses synthesis of 1,5-epoxybenzazocine congeners in 90% yield using catalytic tetrakis(triphenylphosphine)-palladium(0) in acetonitrile containing triethylamine.

Nuss et al., *J. Am. Chem. Soc.* 115, 6991–6992 (1993) discloses synthesis of neocarzinostatin chromophore analogs using catalytic tetrakis(triphenylphosphine)-palladium (0) in THF and alkynyl stannane reactants.

Paquette and Astles, *J. Org. Chem.* 58, 165–169 (1993) discloses synthesis of furanocembranolides with side chain extension mediated by palladium(0) catalyzed coupling to vinylstannane performed in refluxing benzene or dimethoxyethane. The reaction is noted to be solvent-dependent with a change to chloroform being particularly beneficial.

The technical literature also contains a number of disclosures relating to the use of other transition metals in addition to palladium to catalyze reactions. See, e.g., Takagi, *Chemistry Letters*, 2221–2224 (1987), which discloses the use of nickel(0) and palladium(0) complexes as catalysts in the synthesis of diaryl sulfides from aryl halides and aromatic thiols.

None of the above-described references, however, discloses or suggests the particular processes of preparation of the present invention, which are both facile and efficient, while at the same time affording acceptable yields not achievable heretofore.

SUMMARY OF THE INVENTION

The present invention is concerned with several closely related processes of preparation and novel intermediates used therein, where a number of the ultimate products of said processes are known compounds of demonstrated utility as 5-lipoxygenase inhibitors. The present invention additionally concerns a number of other ultimate final products of said processes which have not been known heretofore because they were synthetically inaccessible prior to the availability of said processes and intermediates of the present invention. These novel final products are also useful as 5-lipoxygenase inhibitors, as described in detail further herein. All of said processes of preparation and novel intermediates of the present invention are recited in summary in the paragraphs immediately below.

The present invention is concerned with the compound comprising the novel intermediate tetrahydro-4-[3-(4-fluorophenyl)thio]phenyl-2H-pyran4-carboxamide of Formula (2.0.0):

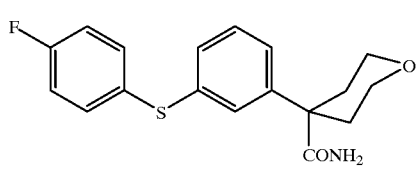

The present invention is further concerned with a process for preparing a compound of Formula (2.0.0) which may be illustrated by the following Synthesis Scheme (10.0.0)

SYNTHESIS SCHEME (10.0.0)

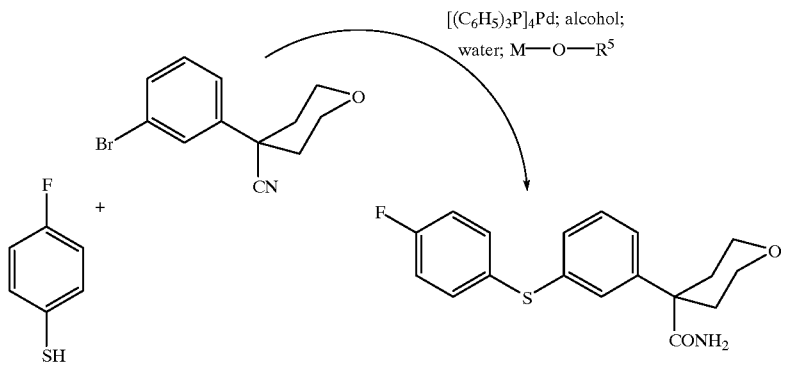

comprising:
(a) establishing a reaction mixture consisting of
(1) tetrahydro-4-(3-bromo- or iodo-phenyl)-2H-pyran-4-nitrile of Formula (3.0.0):

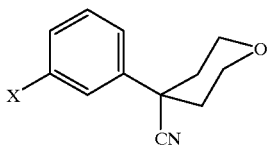

(3.0.0)

where X is bromo or iodo;
and
(2) 4-fluorothiophenol of Formula (4.0.0):

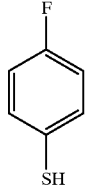

(4.0.0)

(3) in a solvent consisting of a straight or branched chain aliphatic alcohol having a total of from 2 to 7 carbon atoms, optionally as an aqueous mixture thereof; and more preferably where said alcohol is a secondary alcohol selected from the group consisting of iso-propyl alcohol, sec-butyl alcohol, iso-pentyl alcohol, and 2-heptanol, optionally as an aqueous mixture of said secondary alcohol;
(4) in the presence of strong base of Formula (5.0.0):

 (5.0.0)

where
M is an alkali metal, Group 1/Ia element, selected from the group consisting of lithium, Li; sodium,Na; potassium, K; rubidium, Rb; and cesium, Cs; and $R^5$ is hydrogen, H; or straight or branched chain ($C_1$–$C_4$) alkyl; preferably a member selected from the group consisting of lithium hydroxide, LiOH; sodium hydroxide, NaOH; potassium hydroxide, KOH; rubidium hydroxide, RbOH; cesium hydroxide, CsOH; lithium methoxide, $LiOCH_3$; sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium tert-butoxide, $KOC(CH_3)_3$; rubidium tert-butoxide, $RbOC(CH_3)_3$; and cesium tert-butoxide, $CsOC(CH_3)_3$; including mixtures of the above;

and further
(5) in the presence of a transition metal catalyst comprising a palladium metal complex which preferably is a member selected from the group consisting of tetrakis(triphenylphosphine)palladium(0), $[(C_6H_5)_3P]_4Pd(0)$;
tetrakis(methyldiphenylphosphine)palladium(0), $[(C_6H_5)_2PCH_3]_4Pd(0)$;
trans-dichlorobis(methyldiphenylphosphine)palladium(II), $[(C_6H_5)_2PCH_3]_2PdCl_2$;
dichlorobis[methylenebis(diphenylphosphine)]dipalladium-dichloromethane adduct;
dichlorobis(triphenylphosphine)palladium(II), $[(C_6H_5)_3P]_2PdCl_2$;
tris(dibenzylideneacetone)dipalladium(0)-chloroform adduct, $(C_6H_5CH=CHCOCH=CHC_6H_5)_3Pd_2 \cdot CHCl_3$;
bis(dibenzylideneacetone)palladium(0), $(C_6H_5CH=CHCOCH=CHC_6H_5)_2Pd$;
[1,1'-bis(diphenylphosphino)ferrocene]dichloropalladium(II), complex with dichloromethane
bis[1,2-bis(diphenylphosphino)ethane]palladium(0); and
(π-allyl)palladium(II) chloride dimer;
followed by
(b) heating said reaction mixture, preferably at reflux, preferably for a period of from 12 to 36 hours, more preferably from 18 to 24 hours; whereby there is produced said compound of Formula (2.0.0) which is optionally isolated using conventional separation techniques.

The above-described process of preparation in which the 4-carboxamide portion of the pyran moiety is formed during the thio-addition step is a preferred manner of carrying out this portion of the process of the present invention. A useful alternative embodiment comprises formation of the 4-carboxamide portion of the pyran moiety before the step of thio-addtion is carried out. Said alternative embodiment of this portion of the process of the present invention involves a process for preparing a compound of Formula (2.0.0) which may be illustrated by the following Synthesis Scheme (10.1.0):

SYNTHESIS SCHEME (10.1.0)

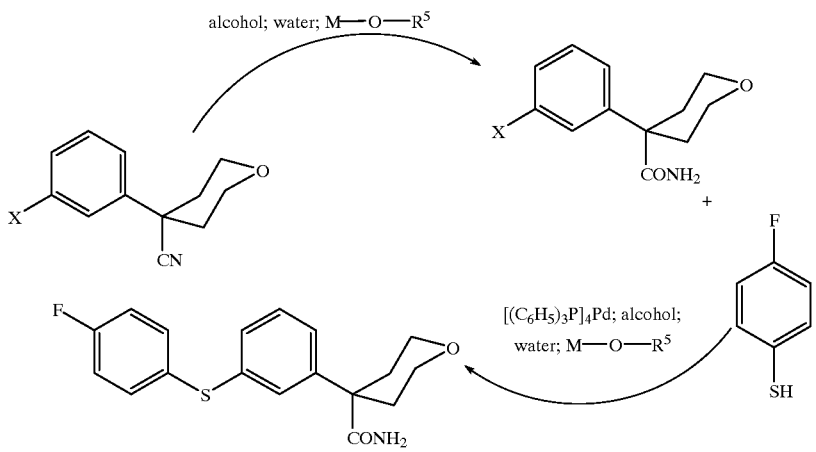

comprising:
(a) establishing a reaction mixture consisting of
   (1) tetrahydro-4-(3-bromo- or iodo-phenyl)-2H-pyran-4-nitrile of Formula (3.0.0):

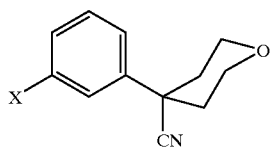

(3.0.0)

where X is bromo or iodo;
(2) in a solvent consisting of an alcohol as defined above, optionally as an aqueous mixture thereof; preferably a secondary alcohol as defined above; more preferably isopropyl alcohol; optionally as an aqueous mixture of said secondary alcohol;
(3) in the presence of strong base of Formula (5.0.0):

M—O—R$^5$  (5.0.0)

where M and R$^5$ are as defined above; preferably wherein said strong base is sodium hydroxide, NaOH; potassium hydroxide, KOH; sodium ethoxide, NaOCH$_2$CH$_3$; or potassium tert-butoxide, KOC(CH$_3$)$_3$;
followed by
(b) heating said reaction mixture, preferably at reflux, preferably for a period of from 3 to 8 hours, more preferably from 5 to 6 hours; whereby there is produced a compound of Formula (3.1.0):

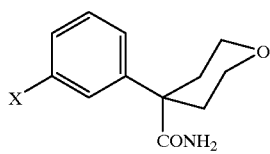

(3.1.0)

where X is bromo or iodo;
followed by (c) forming a reaction mixture consisting of said compound of Formula (3.1.0) and 4-fluorothiophenol of Formula (4.0.0):

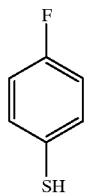

(4.0.0)

(1) in a solvent consisting of an alcohol as defined above, optionally as an aqueous mixture thereof; preferably a secondary alcohol as defined above; more preferably isopropyl alcohol; optionally as an aqueous mixture of said secondary alcohol;
(2) in the presence of a strong base of Formula (5.0.0):

M—O—R$^5$  (5.0.0)

where M and R$^5$ are as defined above; preferably wherein said strong base is sodium hydroxide, NaOH; potassium hydroxide, KOH; sodium ethoxide, NaOCH$_2$CH$_3$; or potassium tert-butoxide, KOC(CH$_3$)$_3$;
and further
(3) in the presence of a transition metal catalyst comprising a palladium metal complex, which is preferably a member selected from the group consisting of tetrakis(triphenylphosphine)palladium(0), [(C$_6$H$_5$)$_3$P]$_4$Pd(0);
tetrakis(methyldiphenylphosphine)palladium(0), [(C$_6$H$_5$)$_2$PCH$_3$]$_4$Pd(0);
trans-dichlorobis(methyldiphenylphosphine)palladium(II), [(C$_6$H$_5$)$_2$PCH$_3$]$_2$PdCl$_2$;
dichlorobis[methylenebis(diphenylphosphine)]dipalladium-dichloromethane adduct;
dichlorobis(triphenylphosphine)palladium(II), [(C$_6$H$_5$)$_3$P]$_2$PdCl$_2$;
tris(dibenzylideneacetone)dipalladium(0)-chloroform adduct, (C$_6$H$_5$CH=CHCOCH=CHC$_6$H$_5$)$_3$Pd$_2$·CHCl$_3$;
bis(dibenzylideneacetone)palladium(0), (C$_6$H$_5$CH=CHCOCH=CHC$_6$H$_5$)$_2$Pd;

[1,1'-bis(diphenylphosphino)ferrocene]dichloropalladium
  (II), complex with dichloromethane
bis[1,2-bis(diphenylphosphino)ethane]palladium(0); and
(π-allyl)palladium(II) chloride dimer;
followed by (d) heating said reaction mixture, preferably at reflux, preferably for a period of from 5 to 15 hours, more preferably from 8 to 10 hours; whereby there is produced said compound of Formula (2.0.0).

The present invention is still further concerned with a process for preparing a compound of Formula (1.3.0):

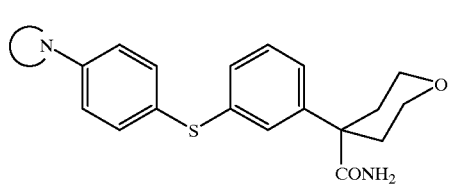
(1.3.0)

which may be illustrated by the following Synthesis Scheme (10.2.0):

SYNTHESIS SCHEME (10.2.0)

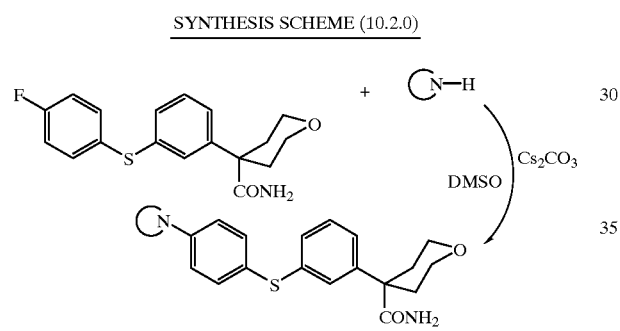

where the moiety of following Formula (1.3.1):

(1.3.1)

is an electron deficient monocyclic or benzo-fused bicyclic N-heterocyclic group containing two nitrogen atoms, of Formula (1.3.2) (1.3.3), (1.3.4) or (1.3.5):

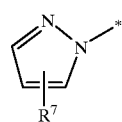
(1.3.2)

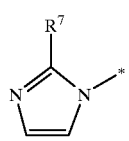
(1.3.3)

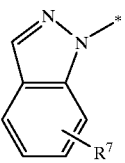
(1.3.4)

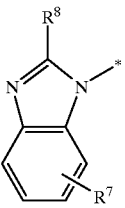
(1.3.5)

where

"*" is a symbol which represents the point of attachment of the moiety of Formula (1.3.2) (1.3.3, (1.3.4) or (1.3.5);

$R^7$ and $R^8$ are independently selected from the group consisting of H; straight or branched chain ($C_1$–$C_4$) alkyl; and ($C_6$–$C_{10}$) aryl; wherein said alkyl and aryl groups are substituted by 0 to 2 substituents selected from the group consisting of halo; hydroxy; cyano; amino; ($C_1$–$C_4$) alkyl; ($C_1$–$C_4$) alkoxy; ($C_1$–$C_4$) alkylthio; ($C_1$–$C_4$) halo-substituted alkyl; ($C_1$–$C_4$) halo-substituted alkoxy; ($C_1$–$C_4$) alkylamino; and di($C_1$–$C_4$) alkylamino;

comprising:

(a) establishing a reaction mixture consisting of
  (1) tetrahydro-4-[3-(4-fluorophenyl)thio]phenyl-2H-pyran-4-carboxamide of Formula (2.0.0):

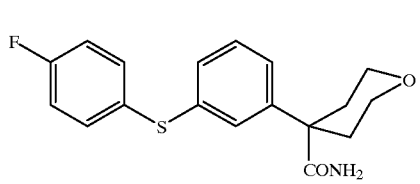
(2.0.0)

and (2) an electron deficient monocyclic or benzo-fused bicyclic N-heterocycle containing two nitrogen atoms, of Formula (1.3.6) (1.3.7), (1.3.8) or (1.3.9):

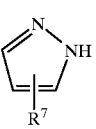
(1.3.6)

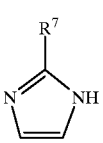
(1.3.7)

-continued (1.3.8)

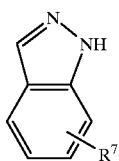

(1.3.9)

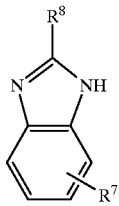

where $R^7$ and $R^8$ have the same meaning as set out above;
(3) in an aprotic solvent, preferably dimethylsulfoxide (DMSO);
(4) in the presence of a carbonate of Formula (5.1.0):

$$(M)_2\text{—}CO_3 \qquad (5.1.0)$$

where M has the same meaning as defined further above, which is preferably cesium carbonate, $Cs_2CO_3$;
followed by
(b) heating said reaction mixture, preferably at reflux, under a nitrogen atmosphere; whereby there is produced a compound of Formula (1.3.0).

The present invention is further concerned with the above-recited method of preparing a compound of Formula (1.3.0), wherein said compound of Formula (1.3.0) is a member selected from the group consisting of:
Tetrahydro-4-{3-[4-(2-methyl-1H-imidazol-1-yl)phenyl]thio}phenyl-2H-pyran-4-carboxamide;
Tetrahydro-4-{3-[4-(1H-imidazol-1-yl)phenyl]thio}phenyl-2H-pyran-4-carboxamide;
Tetrahydro-4-{3-[4-(1H-benzoimidazol-1-yl)phenyl]thio}phenyl-2H-pyran-4-carboxamide;
Tetrahydro-4-{3-[4-(1H-pyrazol-1-yl)phenyl]thio}phenyl-2H-pyran-4-carboxamide; and
Tetrahydro-4-{3-[4-(4-methyl-1H-pyrazol-1-yl)phenyl]thio}phenyl-2H-pyran-4-carboxamide.

The present invention is yet further concerned with the above-mentioned final products which have not been known heretofore because they have been synthetically inaccessible prior to the availability of the processes and intermediates of the present invention. These novel final products are also useful as 5-lipoxygenase inhibitors, and consist of a member selected from the group consisting of:
Tetrahydro-4-{3-[4-(1H-imidazol-1-yl)phenyl]thio}phenyl-2H-pyran-4-carboxamide;
Tetrahydro-4-{3-[4-(1H-benzoimidazol-1-yl)phenyl]thio}phenyl-2H-pyran-4-carboxamide;
Tetrahydro-4-{3-[4-(1H-pyrazol-1-yl)phenyl]thio}phenyl-2H-pyran-4-carboxamide; and
Tetrahydro-4-{3-[4-(4-methyl-1H-pyrazol-1-yl)phenyl]thio}phenyl-2H-pyran-4-carboxamide.

The present invention is still further concerned with a process for preparing a compound of Formula (1.0.0):

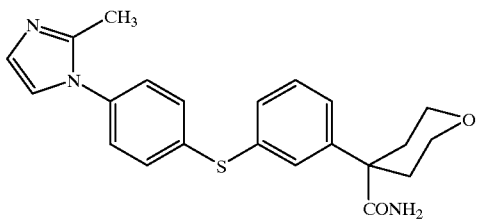

(1.0.0)

comprising:
(a) establishing a reaction mixture consisting of
(1) tetrahydro-4-[3-(4-fluorophenyl)thio]phenyl-2H-pyran-4-carboxamide of Formula (2.0.0):

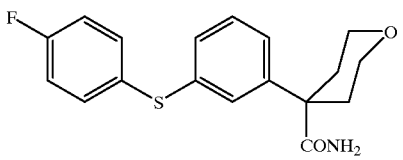

and
(2) 2-methylimidazole;
(3) in an aprotic solvent, preferably dimethylsulfoxide (DMSO);
(4) in the presence of a carbonate of Formula (5.1.0):

$$(M)_2\text{—}CO_3 \qquad (5.1.0)$$

where
M is an alkali metal, Group 1/Ia element, selected from the group consisting of lithium, Li; sodium, Na; potassium, K; rubidium, Rb; and cesium, Cs; preferably cesium carbonate, $Cs_2CO_3$;
followed by
(b) heating said reaction mixture, preferably at reflux, preferably from 115° to 145° C., more preferably from 125° to 130° C., under a nitrogen atmosphere, preferably for from 12 to 30 hours, more preferably for from 17 to 24 hours; whereby there is produced said compound of Formula (1.3.0).

The present invention is still further concerned with a process for preparing a substantially pure mesylate salt of Formula (1.0.1):

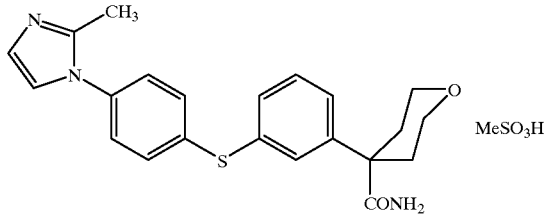

(1.0.1)

which may be illustrated by the following Synthesis Scheme (10.3.0):

SYNTHESIS SCHEME (10.3.0)

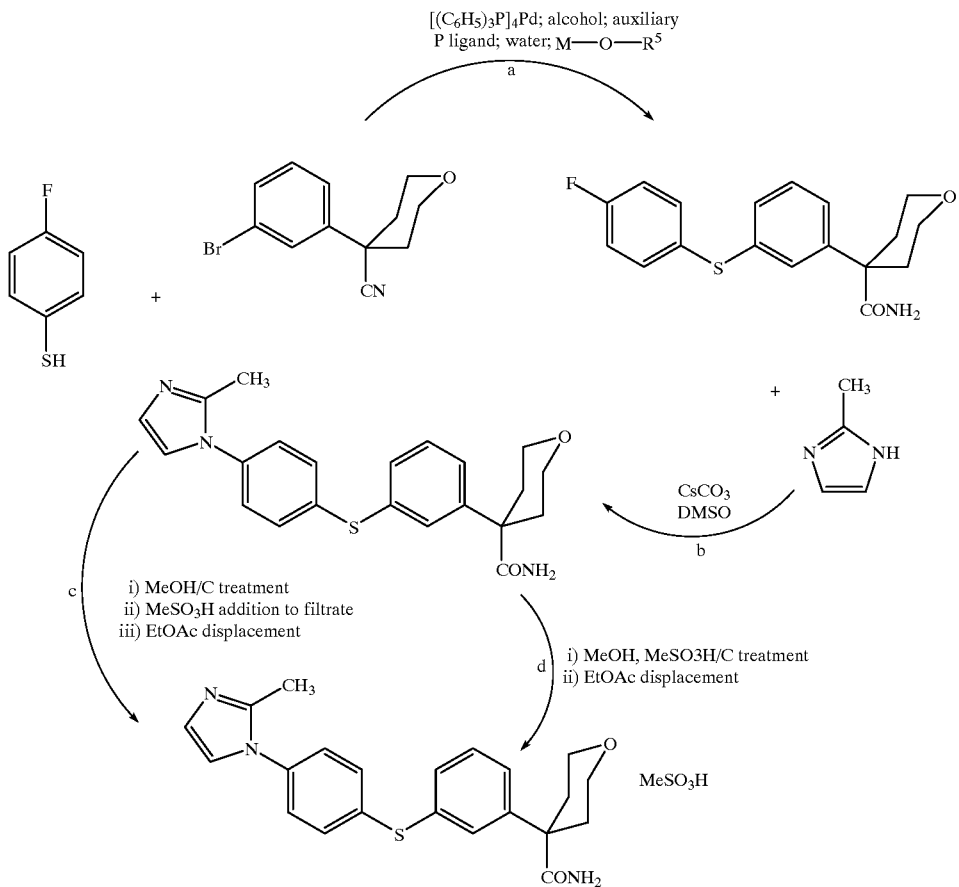

comprising:

(a) preparing a compound of Formula (2.0.0):

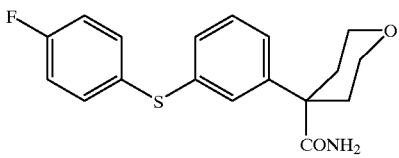

comprising:
(1) establishing a reaction mixture consisting of
(i) tetrahydro-4-(3-bromo-phenyl)-2H-pyran-4-nitrile of Formula (3.2.0):

(3.2.0)

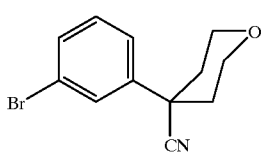

and (ii) 4-fluorothiophenol of Formula (4.0.0):

(4.0.0)

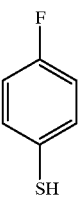

(iii) in a solvent selected from the group consisting of iso-propyl alcohol, sec-butyl alcohol, iso-pentyl alcohol, and 2-heptanol, preferably iso-propyl alcohol, optionally as an aqueous mixture thereof;
(iv) in the presence of a strong base selected from the group consisting of sodium hydroxide, NaOH; and potassium hydroxide, KOH;
and further
(v) in the presence of a transition metal catalyst comprising a member independently selected from the group consisting of palladium metal complexes; preferably wherein said palladium metal complex is a member selected from the group consisting of tetrakis(triphenylphosphine)palladium(0), $[(C_6H_5)_3P]_4Pd(0)$;

tetrakis(methyldiphenylphosphine)palladium(0), [(C$_6$H$_5$)$_2$PCH$_3$]$_4$Pd(0);

trans-dichlorobis(methyldiphenylphosphine)palladium(II), [(C$_6$H$_5$)$_2$PCH$_3$]$_2$PdCl$_2$;

dichlorobis[methylenebis(diphenylphosphine)]dipalladium-dichloromethane adduct;

dichlorobis(triphenylphosphine)palladium(II), [(C$_6$H$_5$)$_3$P]$_2$PdCl$_2$;

tris(dibenzylideneacetone)dipalladium(0)-chloroform adduct, (C$_6$H$_5$CH=CHCOCH=CHC$_6$H$_5$)$_3$Pd$_2$·CHCl$_3$;

bis(dibenzylideneacetone)palladium(0), (C$_6$H$_5$CH=CHCOCH=CHC$_6$H$_5$)$_2$Pd;

[1,1'-bis(diphenylphosphino)ferrocene]dichloropalladium (II), complex with dichloromethane bis[1,2-bis(diphenylphosphino)ethane]palladium(II); and (π-allyl)palladium(II) chloride dimer;

followed by (2) heating said reaction mixture at reflux of from 80° to 84° C. for a period of from 18 to 30 hours, preferably 24 hours; whereby there is produced said compound of Formula (2.0.0);

(b) establishing a reaction mixture consisting of said compound of Formula (2.0.0) and a compound of Formula (1.3.10):

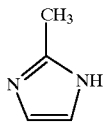

(1.3.10)

(1) in an aprotic solvent which is preferably dimethylsulfoxide (DMSO);

(2) in the presence of cesium carbonate, Cs$_2$CO$_3$;

followed by (c) heating said reaction mixture at reflux, under a nitrogen atmosphere; whereby there is produced a compound of Formula (1.0.0):

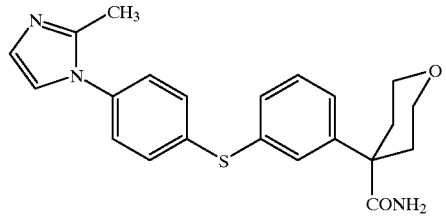

(1.0.0)

followed by (d) forming a concentrated methanol solution of said compound of Formula (1.0.0) which is then filtered, preferably through activated carbon, after which there is then added to the filtrate methanesulfonic acid, MeSO$_3$H; followed by further concentration and the addition of ethyl acetate ad seriatim until a crystalline product is isolated comprising substantially pure mesylate salt of Formula (1.0.1)

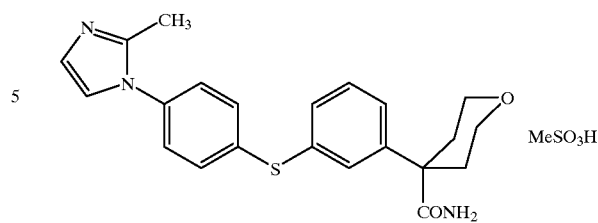

or, alternatively, followed by (e) forming a concentrated methanol solution of said compound of Formula (1.0.0) to which there is then added methanesulfonic acid, MeSO$_3$H; followed by filtering of the mixture, preferably through activated carbon, after which there follows further concentration and the addition of ethyl acetate ad seriatim until a crystalline product is isolated comprising substantially pure mesylate salt of Formula (1.0.1)

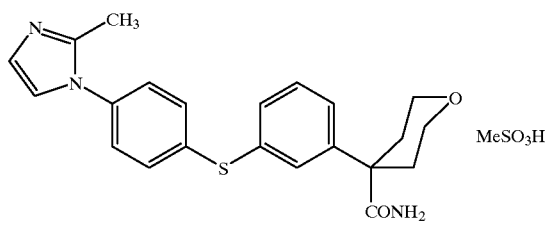

DETAILED DESCRIPTION OF THE INVENTION

The present invention involves an improved process for preparing known compounds of demonstrated utility as a 5-lipoxygenase inhibitors, and in particular the compound of Formula (1.0.0):

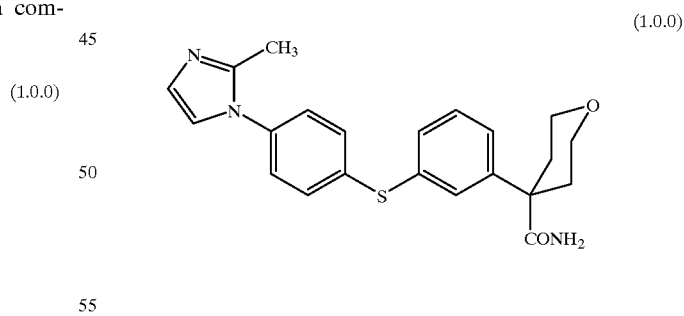

(1.0.0)

Further, the present invention involves preparation of a number of other compounds which have not been known heretofore because they were synthetically inaccessible prior to the availability of the improved process of the present invention. These novel compounds are also useful as 5-lipoxygenase inhibitors, and include, among others, the following compounds of Formulas (1.1.1); (1.1.2); (1.1.3); and (1.1.4):

Tetrahydro-4-{3-[4-(1H-imidazol-1-yl)phenyl]thio}phenyl-2H-pyran-4-carboxamide:

(1.1.1)

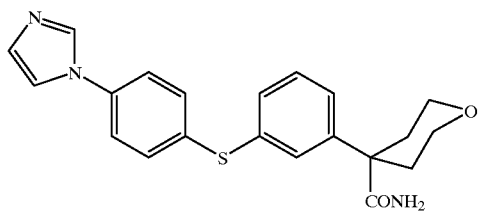

Tetrahydro-4-{3-[4-(1H-benzoimidazol-1-yl)phenyl]thio}phenyl-2H-pyran-4-carboxamide:

(1.1.2)

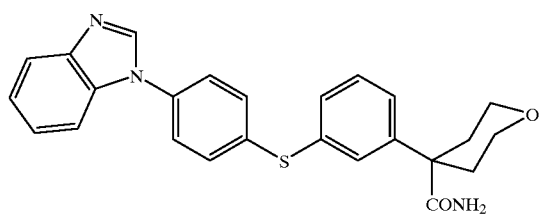

Tetrahydro-4-{3-[4-(1H-pyrazol-1-yl)phenyl]thio}phenyl-2H-pyran-4-carboxamide:

(1.1.3)

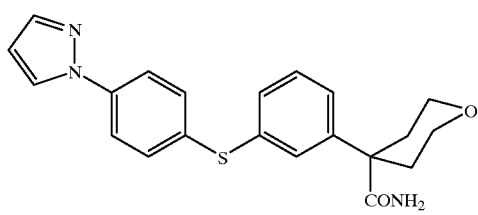

and

Tetrahydro-4-{3-[4-(4-methyl-1H-pyrazol-1-yl)phenyl]thio}phenyl-2H-pyran-4-carboxamide.

(1.1.4)

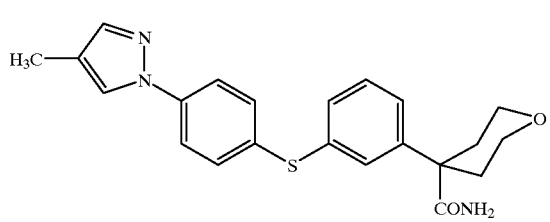

In order to prepare the above-mentioned compounds of Formulas (1.1.1)–(1.1.4) and similar compounds of this type, it is advantageous to use the following process of the present invention for preparing a compound of Formula (1.3.0):

(1.3.0)

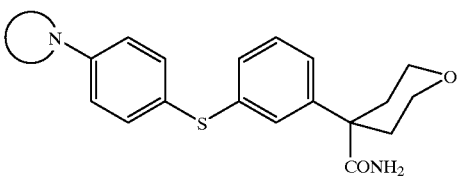

where
the moiety of Formula (1.3.1):

(1.3.1)

is an electron deficient monocyclic or benzo-fused bicyclic N-heterocyclic group containing two nitrogen atoms, of Formula (1.3.2) (1.3.3), (1.3.4) or (1.3.5):

(1.3.2)

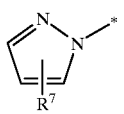

(1.3.3)

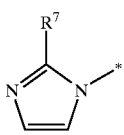

(1.3.4)

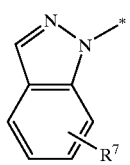

(1.3.5)

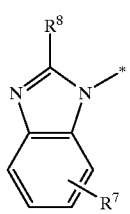

where
"*" is a symbol which represents the point of attachment of the moiety of Formula (1.3.2) (1.3.3), (1.3.4) or (1.3.5);

$R^7$ and $R^8$ are independently selected from the group consisting of H; straight or branched chain ($C_1$–$C_4$) alkyl; and ($C_6$–$C_{10}$) aryl; wherein said alkyl and aryl groups are substituted by 0 to 2 substituents selected from the group consisting of halo; hydroxy; cyano; amino; ($C_1$–$C_4$) alkyl; ($C_1$–$C_4$) alkoxy; ($C_1$–$C_4$) alkylthio; ($C_1$–$C_4$) halo-substituted alkyl; ($C_1$–$C_4$) halo-substituted alkoxy; ($C_1$–$C_4$) alkylamino; and di(($C_1$–$C_4$) alkylamino.

The above-mentioned embodiment of the preparation process of the present invention may be illustrated by following Synthesis Scheme (10.2.0):

SYNTHESIS SCHEME (10.2.0)

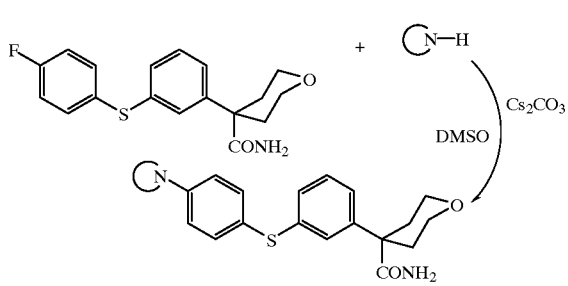

**+where the reactant of Formula (1.4.0):

    (1.4.0)

is an electron deficient monocyclic or benzo-fused bicyclic N-heterocycle containing two nitrogen atoms, of Formula (1.3.6) (1.3.7), (1.3.8) or (1.3.9), as defined further above.

Accordingly, the above-mentioned process of the present invention illustrated in Synthesis Scheme (10.2.0) may be carried out by:

(a) establishing a reaction mixture consisting of
  (1) tetrahydro-4-[3-(4-fluorophenyl)thio]phenyl-2H-pyran-4-carboxamide of Formula (2.0.0):

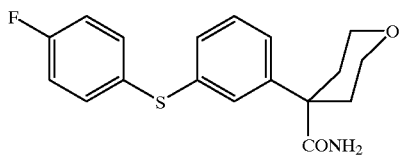

and (2) an electron deficient monocyclic or benzo-fused bicyclic N-heterocycle containing two nitrogen atoms, of Formula (1.3.6) (1.3.7), (1.3.8) or (1.3.9):

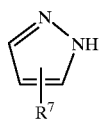    (1.3.6)

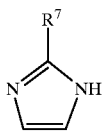    (1.3.7)

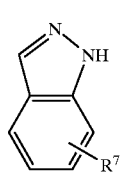    (1.3.8)

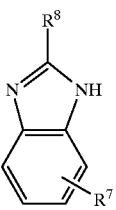    (1.3.9)

where $R^7$ and $R^8$ have the same meaning as set out above;

(3) in an aprotic solvent, preferably a member selected from the group consisting essentially of hexane; 1,4-dioxane; carbon tetrachloride; benzene; toluene; xylenes; diethyl ether; chloroform; ethyl acetate; tetrahydrofuran (THF); methylene chloride; hexamethylphosphoric triamide (HMPT); nitromethane; N,N-dimethylformamide (DMF); acetonitrile; sulfolane; and dimethylsulfoxide (DMSO); more preferably dimethylsulfoxide (DMSO);

(4) in the presence of a carbonate of Formula (5.1.0):

$$(M)_2—CO_3 \quad (5.1.0)$$

where
M is an alkali metal, Group 1/Ia element, selected from the group consisting of lithium, Li; sodium, Na; potassium, K; rubidium, Rb; and cesium, Cs, preferably cesium, Cs;

followed by (b) heating said reaction mixture, preferably at reflux, under a nitrogen atmosphere; whereby there is produced said compound of Formula (1.3.0).

As the person of ordinary skill in the art of preparing organic compounds of the type with which the present invention is concerned will recognize, displacement of aryl fluoride in the presence of base by an electron deficient nitrogen heterocycle is a relatively unknown method of forming carbon-nitrogen bonds, and is clearly one which has not been suggested heretofore as useful in preparing the types of compounds in question. Normally a strong electron withdrawing group, e.g., nitro, positioned para or ortho with respect to the fluorine atom, is required in order to achieve an acceptable level of displacement with a nitrogen nucleophile in the presence of base. Such displacement reactions typically afford only low yields and require elevated reaction temperatures. See, e.g., [INSERT CITATION]. By contrast, the processes of preparation of the present invention give high yields and are carried out at reaction temperatures of 130° C. or less. This result is a wholly unexpected one because the aryl fluoride reactant in the processes of the present invention has no electron withdrawing substituents attached to the aryl ring.

The most preferred solvent for use in the above-described process of the present invention is dimethylsulfoxide (DMSO), although any aprotic solvent is suitable, and those recited above are preferred. In a preferred embodiment of the process, cesium carbonate, $Cs_2CO_3$, is used in the reaction mixture for which DMSO is the solvent. After the reaction mixture is formed, it is heated to reflux under a nitrogen atmosphere. Under most ambient conditions, the reflux temperature of the reaction mixture will be from 120° to 140° C., usually from 125° to 135° C., and most usually 130° C.

A preferred embodiment of the preparation process of the present invention uses cesium carbonate, $Cs_2CO_3$, although any of the other metal carbonates described are suitable. Cesium carbonate is preferred, largely because its greater reactivity provides correspondingly higher yields and thus lower product costs for the reactant of Formula (2.0.0). Cesium carbonate is preferred despite the potential for limited availability due to a relative scarcity of cesium carbonate on the world market. Cesium carbonate provides such excellent end results in the processes of preparation of the present invention that it is considered that new sources of supply would inevitably be located in response to the great demand which would have been established. Nevertheless, the prudent artisan would recognize the risk to maintenance of uninterrupted manufacturing of the compounds prepared by the present invention, or at least the danger of overturning the advantageous economics which such processes currently possess.

It is necessary to heat the reaction mixture at these temperatures for a considerable period of time, from 12 to 30 hours, preferably from 16 to 24 hours, most preferably 18 to 20 hours. The selection of a suitable temperature and time for carrying the reaction to completion are within the skill of the artisan knowledgeable in methods of organic synthesis. Isolation of the product of the above-described process, e.g., by vacuum filtration, washing with water, and drying in a vacuum oven, is accomplished using convention procedures which are likewise a matter of ordinary skill in the art.

It will be noted that in the above-recited process of the present invention, that one of the key reactants is the compound of Formula (2.0.0):

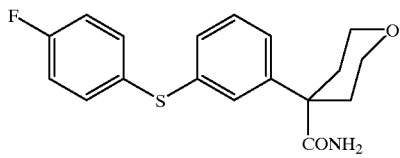

This compound is also a novel intermediate of the present invention, tetrahydro-4-[3-(4-fluorophenyl)thio]phenyl-2H-pyran-4-carboxamide. In order to carry out the above-recited process of the present invention, it is thus necessary to provide a process by which this novel reactant/intermediate itself may be prepared. Accordingly, there follows a description of another process of the present invention by means of which the compound of Formula (2.0.0) is produced.

The present invention is further concerned with a process for preparing a compound of Formula (2.0.0):

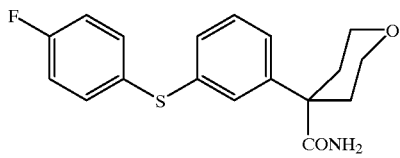

One of the preferred processes of the present invention for preparing the novel intermediate of Formula (2.0.0) may be illustrated by the following Synthesis Scheme (10.0.1):

SYNTHESIS SCHEME (10.0.1)

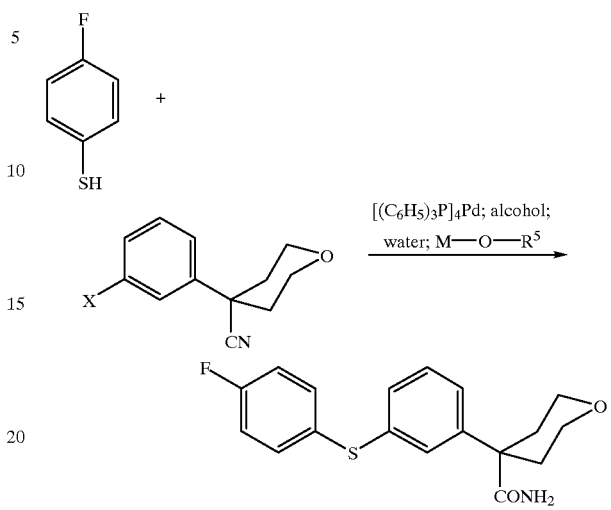

where X, M, and $R^5$ all have the same meaning as defined elsewhere herein.

Accordingly, the above-mentioned process of the present invention illustrated in Synthesis Scheme (10.0.1) may be carried out by:

(a) establishing a reaction mixture consisting of
   (1) tetrahydro-4-(3-bromo- or iodo-phenyl)-2H-pyran-4-nitrile of Formula (3.0.0):

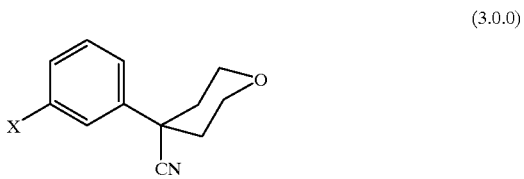

(3.0.0)

where X is bromo or iodo; and
(2) 4-fluorothiophenol of Formula (4.0.0):

(4.0.0)

(3) in a solvent consisting of a straight or branched chain aliphatic alcohol having a total of from 2 to 7 carbon atoms, optionally as an aqueous mixture thereof; and more preferably where said alcohol is a secondary alcohol selected from the group consisting of iso-propyl alcohol, sec-butyl alcohol, iso-pentyl alcohol, and 2-heptanol, optionally as an aqueous mixture of said secondary alcohol;

(4) in the presence of strong base of Formula (5.0.0):

  (5.0.0)

where

M is an alkali metal, Group 1/Ia element, selected from the group consisting of lithium, Li; sodium,Na; potassium, K; rubidium, Rb; and cesium, Cs; and $R^5$ is hydrogen, H; or straight or branched chain $(C_1-C_4)$ alkyl; preferably a member selected from the group consisting of lithium hydroxide, LiOH; sodium hydroxide, NaOH; potassium hydroxide, KOH; rubidium hydroxide, RbOH; cesium hydroxide, CsOH; lithium methoxide, $LiOCH_3$; sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium tert-butoxide, $KOC(CH_3)_3$; rubidium tert-butoxide, $RbOC(CH_3)_3$; and cesium tert-butoxide, $CsOC(CH_3)_3$; including mixtures of the above; and further (5) in the presence of a transition metal catalyst comprising a palladium metal complex, preferably one which is a member selected from the group consisting of tetrakis(triphenylphosphine)palladium(0), $[(C_6H_5)_3P]_4Pd(0)$;

tetrakis(methyldiphenylphosphine)palladium(0), $[(C_6H_5)_2PCH_3·1_4Pd(0)$;

trans-dichlorobis(methyldiphenylphosphine)palladium(II), $[(C_6H_5)_2PCH_3]_2PdCl_2$;

dichlorobis[methylenebis(diphenylphosphine)]dipalladium-dichloromethane adduct;

dichlorobis(triphenylphosphine)palladium(II), $[(C_6H_5)_3P]_2PdCl_2$;

tris(dibenzylideneacetone)dipalladium(0)-chloroform adduct, $(C_6H_5CH=CHCOCH=CHC_6H_5)_3Pd_2·CHCl_3$;

bis(dibenzylideneacetone)palladium(0), $(C_6H_5CH=CHCOCH=CHC_6H_5)_2Pd$;

[1,1'-bis(diphenylphosphino)ferrocene]dichloropalladium (II), complex with dichloromethane bis[1,2-bis(diphenylphosphino)ethane]palladium(II); and (π-allyl)palladium(II) chloride dimer;

followed by (b) heating said reaction mixture, preferably at reflux, preferably for a period of from 12 to 36 hours, more preferably from 18 to 24 hours; whereby there is produced said compound of Formula (2.0.0) which is optionally isolated using conventional separation techniques.

The above-described process is one which prepares an asymmetrically substituted diarylether. At the same time, the reaction which takes place also results in the hydrolysis of the nitrile substituent to the corresponding carboxamide substitutent. It has been found that several factors are important in securing completion of the above-described process with acceptable yields of the novel intermediate of Formula (2.0.0).

One such factor is the solvent in which the reaction involved is carried out. The solvent consists of a straight or branched chain aliphatic alcohol having a total of from 2 to 7 carbon atoms. The alcohol solvent may also be used in admixture with water, ie., as an aqueous mixture of the alcohol in suitable proportions. While the alcohol solvent and water are miscible in almost all proportions, it has been found desirable to maintain the volume to volume ratio of alcohol to water, respectively, in the range of from 25 to 1, to 3 to 1, preferably in the range of from 10 to 1; to 5 to 1.

It has also been found that the most suitable straight or branched chain aliphatic alcohol having a total of from 2 to 7 carbon atoms, for use as the solvent in the process of the present invention is a secondary alcohol selected from the group consisting of iso-propyl alcohol, sec-butyl alcohol, iso-pentyl alcohol, and 2-heptanol. Of these preferred secondary alcohols, the iso-propyl alcohol is the most preferred. The above-mentioned secondary alcohols are also optionally utilized as an aqueous mixture, as described in detail above.

It will be appreciated that the reaction temperature employed in the above-described process of the present invention can be regulated by choosing the alcoholic solvent, depending in turn on the degree of reactivity of the substrate. For example, for the reactant of Formula (3.0.0), where X has the meaning iodo, it has been found that the reaction can be carried out smoothly in refluxing iso-propyl alcohol. For the reactant of Formula (3.0.0), where X has the meaning bromo, it has been found that the reaction can be carried out smoothly in refluxing sec-butyl alcohol. It will also be appreciated that the reaction involving aryl iodide in the above-described process of the present invention, i.e., where X has the meaning iodo in the reactant of Formula (3.0.0), proceeds rapidly and can be completed in a period of a few hours' time. The reaction involving aryl bromide, on the other hand, i.e., where X has the meaning bromo in the reactant of Formula (3.0.0), proceeds more slowly than the reaction involving aryl iodide, and heating of the reaction mixture for a significantly longer period of time, more than 10 hours, is required to complete the reaction. However, prolonged heating of the reaction mixture in the case of either reaction, does not adversely affect the yield of the resulting diaryl thioether, i.e., diaryl sulfide.

Another such factor is the use of a strong base of Formula (5.0.0):

$$M—O—R^5 \qquad (5.0.0)$$

where M is an alkali metal, Group 1/Ia element, selected from the group consisting of lithium, Li; sodium,Na; potassium, K; rubidium, Rb; and cesium, Cs; and $R^5$ is hydrogen, H; or straight or branched chain $(C_1-C_4)$ alkyl. Prefered strong bases comprise a member selected from the group consisting of lithium hydroxide, LiOH; sodium hydroxide, NaOH; potassium hydroxide, KOH; rubidium hydroxide, RbOH; cesium hydroxide, CsOH; lithium methoxide, $LiOCH_3$; sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium tert-butoxide, $KOC(CH_3)_3$; rubidium tert-butoxide, $RbOC(CH_3)_3$; and cesium tert-butoxide, $CsOC(CH_3)_3$.

The above-mentioned strong bases may be used in the form of mixtures thereof, but it is preferred to employ only a single strong base. More preferred among the above-recited strong bases are sodium hydroxide, NaOH; potassium hydroxide, KOH; sodium ethoxide, $NaOCH_2CH_3$; and potassium tert-butoxide, $KOC(CH_3)_3$.

A still further factor in achieving satisfactory completion of the above-described process of the present invention is the use of a transition metal catalyst comprising palladium metal complexes. Included among the palladium metal complexes which are preferred for use in the process of the present invention, are more preferred species of such catalysts which are used in the above-described process. Said more preferred species is a member selected from the group consisting of:

tetrakis(triphenylphosphine)palladium(0): [(C₆H₅)₃P]₄Pd(0);
tetrakis(methyldiphenylphosphine)palladium(0): [(C₆H₅)₂PCH₃]₄Pd(0);
trans-dichlorobis(methyldiphenylphosphine)palladium(II): [(C₆H₅)₂PCH₃]₂PdCl₂;
dichlorobis[methylenebis(diphenylphosphine)]dipalladium-dichloromethane adduct of Formula (6.0.0):

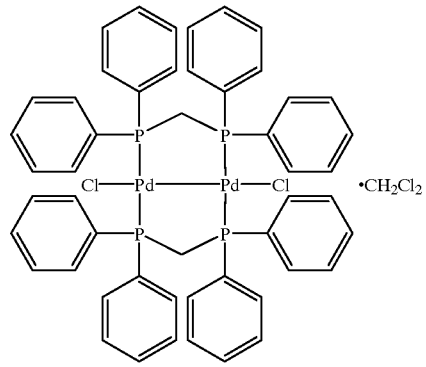

(6.0.0)

dichlorobis(triphenylphosphine)palladium(II): [(C₆H₅)₃P]₂PdCl₂;
tris(dibenzylideneacetone)dipalladium(0)chloroform adduct: (C₆H₅CH=CHCOCH=CHC₆H₅)₃Pd₂·CHCl₃;
bis(dibenzylideneacetone)palladium(0): (C₆H₅CH=CHCOCH=CHC₆H₅)₂Pd;
[1,1'-bis(diphenylphosphino)ferrocene]dichloropalladium(II), complex with dichloromethane, of Formula (6.1.0):

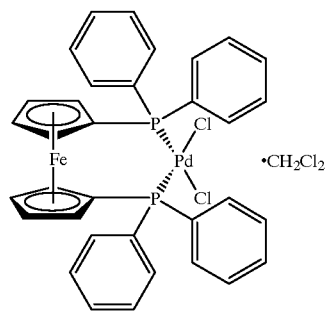

(6.1.0)

bis[1,2-bis(diphenylphosphino)ethane]palladium(II) of Formula (6.2.0):

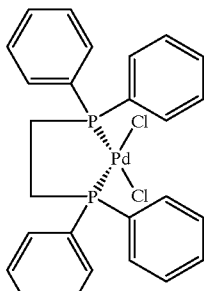

(6.2.0)

and (π-allyl)palladium(II) chloride dimer of Formula (6.3.0):

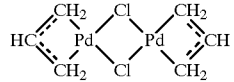

(6.3.0)

Of the palladium metal complexes described above, the most preferred is tetrakis(triphenylphosphine)palladium(0), [(C₆H₅)₃P]₄Pd(0). This preferred catalyst may be used with or without a ligand. When a ligand is used with [(C₆H₅)₃P]₄Pd(0), preferred ligands are triphenylphosphine (TPP), ethylenebis(diphenylphosphine), and tri-(2-tolyl)phosphine, The preferred ratio of catalyst to ligand is approximately 1:2 molar equivalents, but the artisan will be aware that the use of excessive amounts of ligand can lead to a reduction in the overall yield of the reaction in which such a ligand is being used. Other palladium metal complexes used as catalysts in the process of the present invention are used both with and without any ligand. The use of a ligand can have a signficant impact on the yield of final product, i.e., the compound of Formula (2.0.0), as is illustrated by the table of values immediately following showing yields from the above-described process of the present invention where different palladium metal complexes are used without and with a variety of ligands.

TABLE 1

| Ref. No. | Palladium Metal Complex | Ligand | Yield of Compound of Formula (2.0.0) | |
|---|---|---|---|---|
| | | | In-situ | Isolated |
| 1 | trans-dichloro-bis(triphenyl-phosphine) palladium(II) | None | 57.2% | 43.4% |
| 2 | trans-dichloro-bis(triphenyl-phosphine) palladium(II) | Ethylenebis(diphenyl phosphine) | 72.2% | 71.3% |
| 3 | trans-dichloro-bis(triphenyl-phosphine) palladium(II) | Triphenylphosphine | 64.2% | 60.9% |

TABLE 1-continued

| Ref. No. | Palladium Metal Complex | Ligand | Yield of Compound of Formula (2.0.0) | |
|---|---|---|---|---|
| | | | In-situ | Isolated |
| 4 | trans-dichloro-bis(triphenylphosphine) palladium(II) | Tri-(2-tolyl)phosphine | 53.6% | 38.8% |
| 5 | tris(dibenzylideneacetone)-dipalladium(O) chloroform adduct. | None | 7.6% | 5.7% |
| 6 | tris(dibenzylideneacetone)-dipalladium(O) chloroform adduct. | Ethylenebis(diphenyl phosphine) | 34% | 18.3% |
| 7 | tris(dibenzylideneacetone)-dipalladium(O) chloroform adduct. | Triphenylphosphine | 75.1% | 69.8% |
| 8 | dichloro[1,1'-bis(diphenylphosphino)ferrocene] palladium(II) dichloromethane adduct | None | 46.0% | 40.7% |
| 9 | dichloro[1,1'-bis(diphenylphosphino)ferrocene] palladium(II) dichloromethane adduct | Ethylenebis(diphenyl phosphine) | 64.4% | 53.8% |
| 10 | dichloro[1,1'-bis(diphenylphosphino)ferrocene] palladium(II) dichloromethane adduct | Triphenylphosphine | 64.4% | 55.0% |
| 11 | bis(dibenzylideneacetone) palladium(O). | None | 17.5% | 12.4% |
| 12 | bis(dibenzylideneacetone) palladium(O). | Ethylenebis(diphenyl phosphine) | 35.0% | 33.0% |
| 13 | bis(dibenzylideneacetone) palladium(O). | Triphenylphosphine | 55.9% | 39.0% |
| 14 | (π-allyl) palladium(II) chloride dimer. | None | 14.2% | 8.3% |
| 15 | (π-allyl) palladium(II) chloride dimer. | Ethylenebis(diphenyl phosphine) | 43.8% | 33.3% |
| 16 | (π-allyl) palladium(II) chloride dimer. | Triphenylphosphine | 62.4% | 53.7% |
| 17 | tetrakis(triphenylphosphine) palladium(O). CONTROL | None | 71.7% | 71.6% |

The above-described ligands as well as others well known in the art may be employed with the palladium metal complexes used as catalysts in the process of the present invention.

As pointed out further above, a particular advantage of the above-described process is that in the course of carrying out the reaction under the prescribed conditions, both suitable and preferred, the nitrile moiety on the compound of Formula (3.0.0) is hydrolyzed to the corresponding carboxamide group which appears on the final product, a compound of Formula (1.0.0). However, the present invention is also concerned with an alternative process of preparing the novel intermediate, a compound of Formula (2.0.0), in which said nitrile moiety is first hydrolyzed to the corresponding carboxamide, thereby producing a compound of Formula (3.1.0). After this synthesis step has been carried out, the carboxamide compound of Formula (3.1.0) is reacted with the fluorothiophenol compound of Formula (4.0.0) to produce said novel intermediate of Formula (2.0.0).

It will be further noted that the second step of the above-mentioned alternative process is carried out in a fashion which is essentially the same as that illustrated in Scheme 2 above.

Consequently, the present invention is also concerned with an alternative process for preparing a compound of Formula (2.0.0):

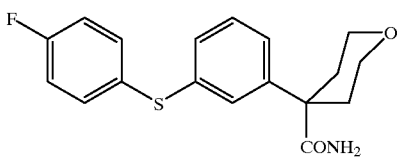

which may be illustrated by SSynthesis Scheme (10.1.0) as follows:

SYNTHESIS SCHEME (10.1.0)

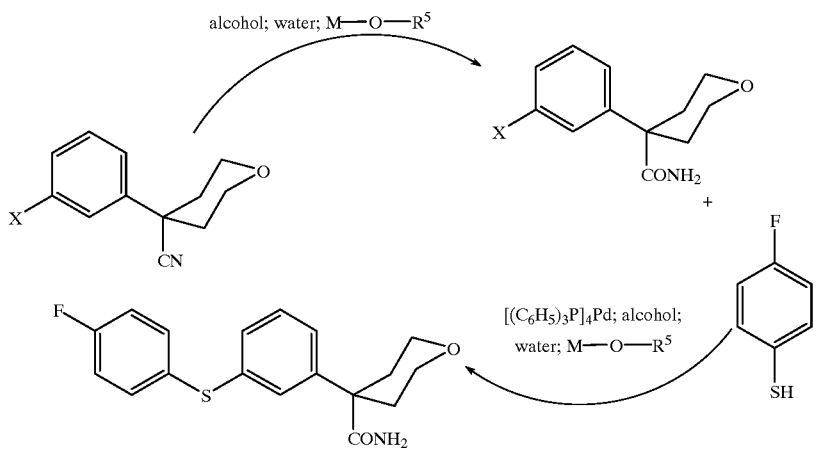

where X, M, and $R^5$ all have the same meaning as defined elsewhere herein.

The alternative process of the present invention illustrated in Synthesis Scheme (10.1.0) may be carried out by:

(a) establishing a reaction mixture consisting of
  (1) tetrahydro-4-(3-bromo- or iodo-phenyl)-2H-pyran-4-nitrile of Formula (3.0.0):

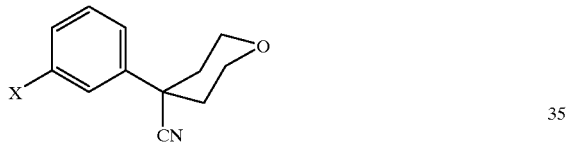
(3.0.0)

where X is bromo or iodo;

(2) in a solvent consisting of a straight or branched chain aliphatic alcohol having a total of from 2 to 7 carbon atoms, optionally as an aqueous mixture thereof; and more preferably where said alcohol is a secondary alcohol selected from the group consisting of iso-propyl alcohol, sec-butyl alcohol, iso-pentyl alcohol, and 2-heptanol, optionally as an aqueous mixture of said secondary alcohol;

(3) in the presence of strong base of Formula (5.0.0):

$$M\text{—}O\text{—}R^5 \quad (5.0.0)$$

where
  M is an alkali metal, Group 1/Ia element, selected from the group consisting of lithium, Li; sodium, Na; potassium, K; rubidium, Rb; and cesium, Cs; and
  $R^5$ is hydrogen, H; or straight or branched chain ($C_1$–$C_4$) alkyl; preferably a member selected from the group consisting of lithium hydroxide, LiOH; sodium hydroxide, NaOH; potassium hydroxide, KOH; rubidium hydroxide, RbOH; cesium hydroxide, CsOH; lithium methoxide, $LiOCH_3$; sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium terf-butoxide, $KOC(CH_3)_3$; rubidium tert-butoxide, $RbOC(CH_3)_3$; and cesium tert-butoxide, $CsOC(CH_3)_3$; including mixtures of the above;

followed by (b) heating said reaction mixture, preferably at reflux, preferably for a period of from 3 to 8 hours, more preferably from 5 to 6 hours; whereby there is produced a compound of Formula (3.1.0):

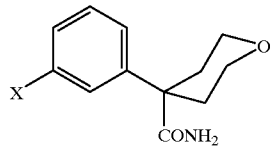
(3.1.0)

where X is bromo or iodo;

followed by (c) forming a reaction mixture consisting of said compound of Formula (4.0.0) and 4-fluorothiophenol of Formula (4.0.0):

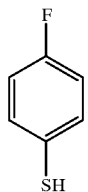
(4.0.0)

(1) in a solvent consisting of a straight or branched chain aliphatic alcohol having a total of from 2 to 7 carbon atoms, optionally as an aqueous mixture thereof; and more preferably where said alcohol is a secondary alcohol selected from the group consisting of iso-propyl alcohol, sec-butyl alcohol, iso-pentyl alcohol, and 2-heptanol, optionally as an aqueous mixture of said secondary alcohol;

(2) in the presence of strong base of Formula (5.0.0):

$$M\text{—}O\text{—}R^5 \quad (5.0.0)$$

where
  M is an alkali metal, Group 1/Ia element, selected from the group consisting of lithium, Li; sodium, Na; potassium, K; rubidium, Rb; and cesium, Cs; and R[5] is hydrogen, H; or straight or branched chain ($C_1$–$C_4$) alkyl; preferably a member selected from the group consisting of lithium hydroxide, LiOH; sodium hydroxide, NaOH; potassium hydroxide, KOH; rubidium hydroxide, RbOH; cesium hydroxide, CsOH; lithium methoxide, $LiOCH_3$; sodium methoxide, $NaOCH_3$; potassium methoxide, $KOCH_3$; rubidium methoxide, $RbOCH_3$; cesium methoxide, $CsOCH_3$; lithium ethoxide, $LiOCH_2CH_3$; sodium ethoxide, $NaOCH_2CH_3$; potassium ethoxide, $KOCH_2CH_3$; rubidium ethoxide, $RbOCH_2CH_3$; cesium ethoxide, $CsOCH_2CH_3$; lithium tert-butoxide, $LiOC(CH_3)_3$; sodium tert-butoxide, $NaOC(CH_3)_3$; potassium tert-butoxide, $KOC(CH_3)_3$; rubidium tert-butoxide, $RbOC(CH_3)_3$; and cesium tert-butoxide, $CsOC(CH_3)_3$; including mixtures of the above; and further (3) in the presence of a transition metal catalyst comprising a member independently selected from the group consisting of palladium metal complexes; preferably wherein said palladium metal complex is a member selected from the group consisting of tetrakis(triphenylphosphine)palladium(0), $[(C_6H_5)_3P]_4Pd(0)$;
tetrakis(methyldiphenylphosphine)palladium(0), $[(C_6H_5)_2PCH_3]_4Pd(0)$;
trans-dichlorobis(methyldiphenylphosphine)palladium(II), $[(C_6H_5)_2PCH_3]_2PdCl_2$;
dichlorobis[methylenebis(diphenylphosphine)]dipalladium-dichloromethane adduct;
dichlorobis(triphenylphosphine)palladium(II), $[(C_6H_5)_3P]_2PdCl_2$;
tris(dibenzylideneacetone)dipalladium(0)-chloroform adduct, $(C_6H_5CH=CHCOCH=CHC_6H_5)_3Pd_2·CHCl_3$;
bis(dibenzylideneacetone)palladium(0), $(C_6H_5CH=CHCOCH=CHC_6H_5)_2Pd$;
[1,1'-bis(diphenylphosphino)ferrocene]dichloropalladium (II), complex with dichloromethane
bis[1,2-bis(diphenylphosphino)ethane]palladium(II); and
(π-allyl)palladium(II) chloride dimer;
followed by (d) heating said reaction mixture, preferably at reflux, preferably for a period of from 5 to 15 hours, more preferably from 8 to 10 hours; whereby there is produced said compound of Formula (2.0.0).

One of the key aspects of the preparation processes of the present invention is an improved means of producing the known 5-lipoxygenase inhibitory compound of Formula (1.0.0):

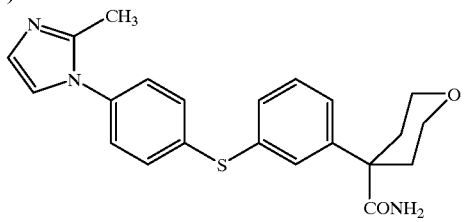

This improved process involves most of the above-described preferred embodiments of the present invention, and may be illustrated by SSynthesis Scheme (10.3.1) as follows:

SYNTHESIS SCHEME (10.3.1)

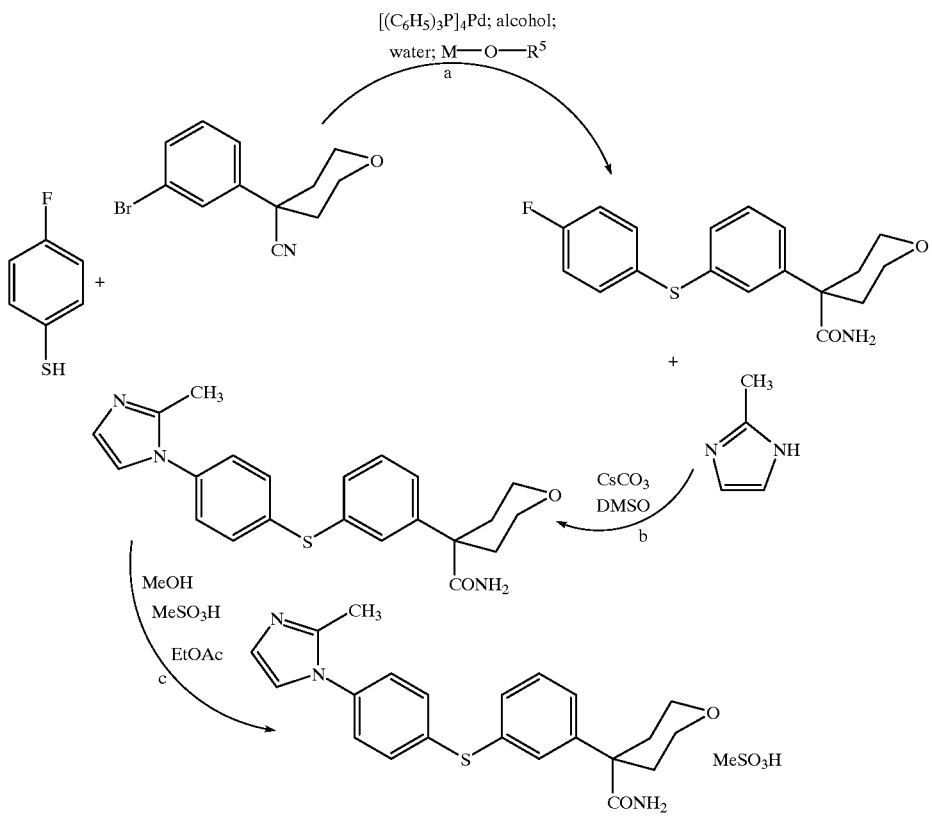

The improved process of the present invention illustrated in Synthesis Scheme (10.3.1) is deemed to comprise a total of six embodiments of the present invention. The first embodiment is Step a, which is the first step illustrated in Synthesis Scheme (10.3.1), and is a process for preparing the novel intermediate of the present invention of Formula (2.0.0). The second embodiment is Step b, which is the second or middle step illustrated in Synthesis Scheme (10.3.1), and is a process for preparing the known 5-lipoxygenase inhibitory compound of Formula (1.0.0), as the compound per se. The third embodiment is Step c, which is the last step in Synthesis Scheme (10.3.1), and is a process for preparing the mesylate salt of said known compound of Formula (1.0.0). The fourth embodiment is Step b+Step c. The fifth embodiment is Step a+Step b. The sixth embodiment is Step a+Step b+Step c.

For the sake of brevity, only the second and sixth embodiments are described in detail below. Accordingly, the second above-mentioned embodiment, Step b in Synthesis Scheme (10.3.1), is carried out as follows:

(a) establishing a reaction mixture consisting of
  (1) tetrahydro-4-[3-(4-fluorophenyl)thio]phenyl-2H-pyran-4-carboxamide of Formula (2.0.0):

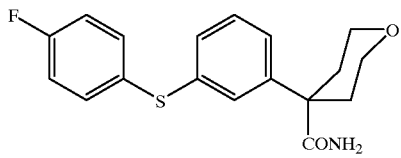

and
  (2) 2-methylimidazole;
  (3) in an aprotic solvent, preferably a member selected from the group consisting essentially of hexane; 1,4-dioxane; carbon tetrachloride; benzene; toluene; xylenes; diethyl ether; chloroform; ethyl acetate; tetrahydrofuran (THF); methylene chloride; hexamethylphosphoric triamide (HMPT); nitromethane; N,N-dimethylformamide (DMF); acetonitrile; sulfolane; and dimethylsulfoxide (DMSO); more preferably dimethylsulfoxide (DMSO);
  (4) in the presence of a carbonate of Formula (5.1.0):

$$(M)_2\text{—}CO_3 \qquad (5.1.0)$$

where
  M is an alkali metal, Group 1/Ia element, selected from the group consisting of lithium, Li; sodium, Na; potassium, K; rubidium, Rb; and cesium, Cs; preferably cesium carbonate, $Cs_2CO_3$;
  followed by
(b) heating said reaction mixture, preferably at reflux, preferably from 115° to 145° C., more preferably from 125° to 130° C., under a nitrogen atmosphere, preferably for from 12 to 30 hours, more preferably for from 17 to 24 hours; whereby there is produced said compound of Formula (1.3.0).

The above-mentioned sixth embodiment, Step a+Step b+Step c of Synthesis Scheme (10.3.1), of the present invention is a process for preparing a substantially pure mesylate salt of Formula (1.0.1):

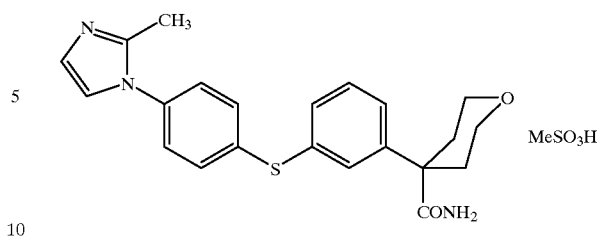

comprising:

(a) preparing a compound of Formula (2.0.0):

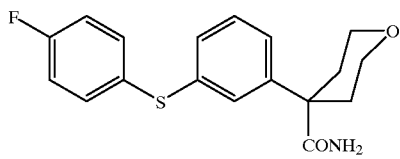

comprising:
  (1) establishing a reaction mixture consisting of
    (i) tetrahydro-4-(3-bromo-phenyl)-2H-pyran-4-nitrile of Formula (3.2.0):

(3.2.0)

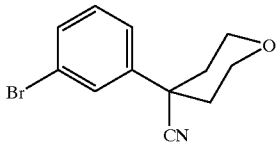

and
    (ii) 4-fluorothiophenol of Formula (4.0.0):

(4.0.0)

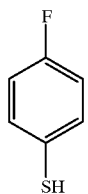

(iii) in a solvent selected from the group consisting of iso-propyl alcohol, sec-butyl alcohol, iso-pentyl alcohol, and 2-heptanol, optionally as an aqueous mixture thereof;
    (iv) in the presence of a strong base selected from the group consisting of sodium hydroxide, NaOH; and potassium hydroxide, KOH;
    and further
    (v) in the presence of a catalyst comprising a member selected from the group consisting of:
tetrakis(triphenylphosphine)palladium(0), $[(C_6H_5)_3P]_4Pd(0)$;
tetrakis(methyldiphenylphosphine)palladium(0), $[(C_6H_5)_2PCH_3]_4Pd(0)$;

trans-dichlorobis(methyldiphenylphosphine)palladium(II), [(CrH₅)₂PCH₃]₂PdCl₂;
dichlorobis[methylenebis(diphenylphosphine)]dipalladium-dichloromethane adduct;
dichlorobis(triphenylphosphine)palladium(II), [C₆H₅)₃P]₂PdCl₂;
tris(dibenzylideneacetone)dipalladium(0)-chloroform adduct, (C₆H₅CH=CHCOCH=CHC₆H₅)₃Pd₂.CHCl₃;
bis(dibenzylideneacetone)palladium(0), (C₆H₅CH=CHCOCH=CHC₆H₅)₂Pd;
[1,1'-bis(diphenylphosphino)ferrocene]dichloropalladium (II), complex with dichloromethane
bis[1,2-bis(diphenylphosphino)ethane]palladium(II); and
(π-allyl)palladium(II) chloride dimer;
followed by (2) heating said reaction mixture at reflux of from 80° to 84° C. for a period of from 18 to 30 hours, preferably 24 hours; whereby there is produced said compound of Formula (2.0.0);

(b) establishing a reaction mixture consisting of said compound of Formula (2.0.0) and a compound of Formula (1.3.10):

(1.3.10)

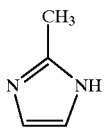

(1) in an aprotic solvent selected from the group consisting essentially of tetrahydrofuran (THF); methylene chloride; N,N-dimethylformamide (DMF); and dimethylsulfoxide (DMSO); more preferably dimethylsulfoxide (DMSO);

(2) in the presence of cesium carbonate, Cs₂CO₃; followed by (c) heating said reaction mixture at reflux, under a nitrogen atmosphere; whereby there is produced a compound of Formula (1.0.0):

(1.0.0)

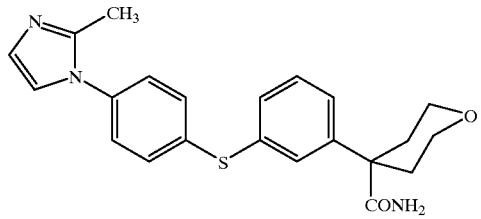

followed by (d) forming a concentrated methanol solution of said compound of Formula (1.0.0) to which there is then added methanesulfonic acid, MeSO₃H; followed by further concentration and the addition of ethyl acetate ad seratim until a crystalline product is isolated comprising substantially pure mesylate salt of Formula (1.0.1)

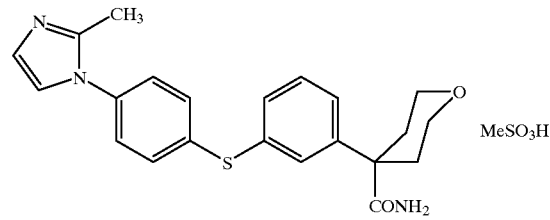

or, alternatively, followed by (e) forming a concentrated methanol solution of said compound of Formula (1.0.0) to which there is then added methanesulfonic acid, MeSO₃H; followed by filtering of the mixture, preferably through activated carbon, after which there follows further concentration and the addition of ethyl acetate ad seriatim until a crystalline product is isolated comprising substantially pure mesylate salt of Formula (1.0.1).

It will be appreciated that the above-described process for preparing the mesylate salt of the compound of Formula (1.0.0) may be readily adapted using the skills and knowledge available in the art, to prepare other, analogous sulfonate salts of the compound of Formula (1.0.0), especially the tosylate salt.

EXEMPLIFICATION OF PREFERRED EMBODIMENTS

The processes, novel intermediate, and novel final products of the present invention will be better appreciated by their illustration in working examples showing details for carrying them out. However, the examples of preferred embodiments of the present invention which follow are intended for purposes of demonstration only, and should not be taken as in any way limiting the scope of the present invention, for which purpose the claims appended hereto are set forth.

EXAMPLE 1

Synthesis of tetrahydro-4-(3-bromophenyl)-2H-pyran-4-nitrile

3-Bromophenylacetonitrile (20.0 g, 102 mmole, 1 eq.), tetrahydrofuran (120 ml), 40% aqueous sodium hydroxide solution (180 ml, mmole, eq.), tetrabutylammonium hydrogensulfate (3.46 g, mmole, 0.1 eq.) were stirred in a reaction flask set for boiling at reflux. Thereafter, 2,2'-dichlorodiethylether (13.75 ml, 117.3 mmole, 0.1 eq.) was added with stirring at room temperature, 20–25° C. The resultant reaction mixture was boiled at reflux for 5–8 h at approximately 64° C. The reaction mixture was cooled to ambient temperature and ethyl acetate (154 ml) was added. The lower aqueous layer was separated and the organic layer evaporated down into a red oil. Iso-propanol (100 ml) and water (10 ml) were added to the oil and stirred at 0° C. overnight to yield a crystal slurry. The crystal slurry was vacuum filtered, washed with isopropanol (2×20 ml). The white crystalline solid was dried under vacuum at 40–45° C. Yield 18.57 g (68.4%): mp 82–85° C.; m/z 267 (m+1); ¹H NMR (300 MHz, DMSO) δ7.75 (s, 1H), 7.6 (m, 2H), 7.44 (t, 1H), 4.02 (m, 2H), 3.66 (m, 2H), 2.14 (m, 4H).

EXAMPLE 2
Synthesis of tetrahydro-4-[3-(4-fluorophenyl)thio]phenyl-2H-pyran-4-carboxamide Propan-2-ol (311 ml), tetrahydro-4-(3-bromophenyl)-2H-pyran-4-nitrile (51.91 g, 0.195 mole, 1 eq.), potassium hydroxide (25.16 g, 0.39 mole, 2 eq.), water (4 ml, 0.39 mole, 2 eq.), tetrakis(triphenylphosphine)palladium(0) (2.26 g, 0.00195 mole, 0.01 eq.) and 4-fluorothiophenol (25 g, 0.195 mole, 1 eq.) were added to a reaction flask set for boiling at reflux under a nitrogen atmosphere. The resultant reaction mixture was boiled at reflux for 20–24 h at approximately 82° C. The reaction mixture was cooled to ambient temperature, 20–25° C. and water (315 ml) was added to obtain a slurry. The crude product was isolated by filtration and washed with 1:1 water: propan-2-ol (125 ml) and sucked dry. Crude dry product was dissolved in methanol (1900 ml), treated with activated charcoal, Darco KB-B (2.5 g) and Celite filter aid (10 g) at reflux temperature, approximately 60° C., for 20 min., filtered free of charcoal and filter aid. The filter cake was washed with hot methanol (200 ml) and the wash combined with the main filtrate. The product containing combined filtrate and wash was concentrated by distillation to a volume of approximately 700 ml. The concentrate was cooled to 10–0° C., granulated in this temperature range for 1–3 h to establish crystal formation. The product crystals were isolated by filtration, washed with cold methanol (125 ml) and dried under vacuum at 40–45° C. Yield 40.2 g (62.2%): mp 175–178° C.; m/z 332 (m+1); $^1$H NMR (300 MHz, DMSO) δ7.37 (m, 8H), 7.11 (m, 2H), 3.60 (m, 2H), 2.30 (m, 2H), 2.40 (m, 2H), 1.77 (m, 2H); IR (drifts) $v_{max}$ 3394, 3198, 3078, 3014, 2970, 2931, 2880, 2824, 1681, 1664, 1664, 1623, 1588, 1569.

EXAMPLE 3
Synthesis of tetrahydro-4-[3-[4-(2-methyl-1H-imidazol-1-yl)phenyl]thio]phenyl-2H-pyran-4-carboxamide Tetrahydro-4-[3-(4-fluorophenyl)thio]phenyl-2H-pyran-4-carboxamide (25.0 g, 75.4 mmole, 1 eq), dimethylsulfoxide (250 ml, 10 vol), 2-methylimidazole (12.39 g, 150.9 mmole, 2.0 eq) and cesium carbonate (49.16 g, 150.9 mmole, 2.0 eq) were added to a reaction flask set for boiling at reflux under a nitrogen atmosphere, and the reaction mixture was heated at 125–130° C. for 17–24 h under nitrogen. After the reaction was completed it was cooled (<30° C.) and quenched with water (250 ml, 10 vol), which resulted in formation of a precipitate. An exotherm of 10–15° C. was observed during the water addition. The reaction slurry so formed, was cooled to room temperature (15–25° C.) and then granulated for 1 h. The product was isolated by vacuum filtration and washed with water (175 ml, 7 vol). The product was dried overnight in a vacuum oven at 40–45° C. Yield 27.85 g, 94%: mp 198–200° C.; m/z 396 (m+1); $^1$H NMR (300 MHz, DMSO) δ7.41 (m, 10H), 7.12 (s, 1H), 6.93 (d, 1H), 3.75 (m, 2H), 3.48 (t, 2H), 2.48 (d, 2H), 2.3 (s, 3H), 1.75 (m, 2H); IR (drifts) $v_{max}$ 3402, 3301, 3123, 3096, 2971, 2930, 2880, 1680, 1663, 1622, 1593, 1569, 1528.

EXAMPLE 4
Mesylate Salt Formation

Methanol (640 ml, 40 vol), tetrahydro-4-[3-[4-(2-methyl-1H-imidazol-1-yl) phenyl]thio]phenyl-2H-pyran-4-carboxamide prepared by the method of Example 3 (16.0 g, 40.7 mmol, 1.0 eq.), activated charcoal, Darco KB-B (0.80 g) and filter aid, Celite (2.4 g) were added to a reaction flask set for boiling at reflux. The mixture was heated to reflux, approximately 66° C. to dissolve the organic substrate. The contents of the reaction flask were cooled to the temperature range 55–60° C., and the carbon and filter aid removed by filtration in the temperature range 55–60° C. The residue was washed with methanol (50 ml) and the wash combined with the original filtrate. The resultant clear combined filtrate and wash so obtained was concentrated by distillation at atmospheric pressure to a volume of approximately 700 ml. Methanesulfonic acid (4.1 g, 42.7 mmol, 1.05 eq.) was added to the concentrated methanol solution. The resultant solution was further concentrated by distillation at atmospheric pressure to a volume of about 250 ml and ethyl acetate (500 ml) was added in two aliquots, the net volume was reduced by distillation to 250 ml after each ethyl acetate addition. The resultant crystal slurry was cooled to room temperature 15–25° C. and granulated from 4–16 h in the temperature range 15–25° C. The white crystalline product was isolated by filtration and washed with ethyl acetate (135 ml), and dried under vacuum at 45–50° C. Yield 18.39 g, 92.3%. The salt so produced is characterized by an X-ray powder diffraction pattern with principal peaks set forth in Table 2 below:

TABLE 2

| Peak Number | 2θ(Gk. Theta)° | d-space(Å) | Peak Number | 2θ(Gk. Theta)° | d-space(Å) |
|---|---|---|---|---|---|
| 1 | 6.5 | 13.6 | 20 | 24.0 | 3.7 |
| 2 | 9.1 | 9.7 | 21 | 24.55 | 3.6 |
| 3 | 13.35 | 6.6 | 22 | 25.4 | 3.5 |
| 4 | 14.2 | 6.2 | 23 | 26.1 | 3.4 |
| 5 | 14.4 | 6.1 | 24 | 26.7 | 3.3 |
| 6 | 15.1 | 5.9 | 25 | 27.7 | 3.2 |
| 7 | 15.4 | 5.7 | 26 | 28.65 | 3.1 |
| 8 | 16.0 | 5.5 | 27 | 29.3 | 3.0 |
| 9 | 16.7 | 5.3 | 28 | 30.0 | 3.0 |
| 10 | 17.2 | 5.1 | 29 | 30.5 | 2.9 |
| 11 | 17.85 | 5.0 | 30 | 31.7 | 2.8 |
| 12 | 18.25 | 4.85 | 31 | 32.8 | 2.7 |
| 13 | 19.0 | 4.7 | 32 | 33.8 | 2.65 |
| 14 | 19.9 | 4.4 | 33 | 35.3 | 2.5 |
| 15 | 21.0 | 4.2 | 34 | 36.0 | 2.5 |
| 16 | 22.0 | 4.0 | 35 | 36.7 | 2.4 |
| 17 | 22.3 | 4.0 | 36 | 37.6 | 2.4 |
| 18 | 22.9 | 3.9 | 37 | 39.2 | 2.3 |
| 19 | 23.6 | 3.8 | | | |

EXAMPLE 5
Recrystallization of tetrahydro-4-[3-[4-(2-methyl-1H-imidazol-1-yl)phenyl]thio]phenyl-2H-pyran-4-carboxamide Methanol (3200 ml, 40 vol), tetrahydro-4-[3-[4-(2-methyl-1H-imidazol-1-yl) phenyl]thio]phenyl-2H-pyran-4-carboxamide prepared by the method of Example 3, (80.2 g), activated charcoal, Darco KB-B (4.0 g) and filter aid, Celite (10 9) were added to a reaction flask set for boiling at reflux. The mixture was heated to reflux, approximately 66° C. to dissolve the organic substrate. The contents of the reaction flask were cooled to the temperature range 55–60° C., and the carbon and filter aid removed by filtration in the temperature range 55–60° C. The residue was washed with methanol (300 ml) and the wash combined with the original filtrate. The resultant clear combined filtrate and wash so obtained was concentrated by distillation at atmospheric pressure to a volume of approximately 1000 ml. The methanol concentrate so obtained was cooled to the temperature range 3–7° C. to establish product crystallization and granulated for 6–24 hours in this temperature range. The white product crystals were isolated by filtration and dried under vacuum at 40–45° C. Yield 70.3 g, 87.7%. mp 198–200° C.; m/z 396 (m+1); Spectral data as in Example 3.

EXAMPLE 6

Synthesis of tetrahydro-4-[3-[4-(1H-imidazol-1-yl)phenyl]thio]phenyl-2H-pyran-4-carboxamide Tetrahydro-4-[3-(4-fluorophenyl)thio]phenyl-2H-pyran-4-carboxamide (2.0 g, 6.02 mmole, 1 eq), dimethylsulfoxide (20 ml, 10 vol), imidazole (0.822 g, 12.07 mmole, 2.0 eq) and cesium carbonate (3.93 g, 12.07 mmole, 2.0 eq) were added to a reaction flask set for boiling at reflux under a nitrogen atmosphere, and the reaction mixture was heated with stirring at 139–142° C. for 5 hours under nitrogen. After completion, the reaction was cooled (<30° C.) and quenched with water (20 ml, 10 vol). This resulted in formation of a precipitate. An exotherm of 10–15° C. was observed during the water addition. The reaction slurry so formed, was cooled to room temperature (15–25° C.) and then granulated for 1 h. The product was isolated by vacuum filtration and washed with water (20 ml, 10 vol) to obtain the crude product, which was dried overnight in a vacuum oven at 40° C. The dried solid was dissolved in water (200 ml) that was adjusted to pH 2 using 6N dilute hydrochloric acid, and then extracted with dichloromethane (3×50 ml). The product containing aqueous layer was adjusted to pH 14 with 50% aqueous sodium hydroxide, to precipitate product. The resultant slurry was granulated for 5 h, then vacuum filtered and dried to obtain a white solid (1.76 g, 77%): mp 176–178° C.; m/z 380 (m+1); (Found: C, 65.94; H, 5.45; N, 10.76; S, 8.56. $C_{21}H_{21}N_3O_2S$ requires C, 66.47; H, 5.58; N, 11.07; S, 8.45.) $^1H$ NMR (300 MHz, DMSO) δ8.32 (s, 1H), 7.80 (s, 1H), 7.70 (d, 2H), 7.44 (m, 3H), 7.26 (d, 3H), 7.22 (s, 1H), 7.21 (d, 1H), 7.13 (d, 2), 3.7 (m, 2H), 3.49 (t, 2H), 2.44 (d, 2H), 1.81 (m, 2H); $^{13}C$ NMR (75 MHz, DMSO) δ175.9, 14.15, 137.25, 136.80, 135.62, 134.39, 133.09, 131.30, 130.95, 130.25, 129.54, 126.41, 122.52, 119.15, 65.93, 49.06, 35.21; IR (drifts) $v_{max}$ 3381, 3177, 1684, 1667, 1508.

EXAMPLE 7

Synthesis of tetrahydro-4-[3-[4-(1H-pyrazol-1-yl)phenyl]thio]phenyl-2H-pyran-4-carboxamide Tetrahydro-4-[3-(4-fluorophenyl)thio]phenyl-2H-pyran-4-carboxamide (2.0 g, 6.02 mmole, 1 eq), dimethylsulfoxide (20 ml, 10 vol), pyrazole (0.822 g, 12.07 mmole, 2.0 eq) and cesium carbonate (3.93 g, 12.07 mmole, 2.0 eq) were added to a reaction flask set for boiling at reflux under a nitrogen atmosphere, and the reaction mixture was heated with stirring at 139–142° C. for 5 hours under nitrogen. After completion, the reaction was cooled (<30° C.) and quenched with water (20 ml, 10 vol). This resulted in formation of a precipitate. An exotherm of 10–15° C. was observed during the water addition. The reaction slurry so formed, was cooled to room temperature (15–25° C.) and then granulated for 1 h. The product was isolated by vacuum filtration and washed with water (20 ml, 10 vol) to obtain the crude product, which was dried overnight in a vacuum oven at 40° C. The crude product was dissolved in methanol (290 ml) to form a solution which was filtered and then concentrated to initiate crystallization, after a period of granulation at room temperature, product was isolated by filtration and dried to obtain a white solid (1.5 g, 65%): mp 196–198° C.; m/z 380 (m+1); (Found: C, 66.09; H, 5.6; N, 10.87; S, 9.06. $C_{21}H_{21}N_3O_2S$ requires C, 66.47; H, 5.58; N, 11.07; S, 8.45.) $^1$NMR (300 MHz, DMSO) δ8.55 (d, 1H), 7.89 (d, 2H), 7.79 (s, 1H), 7.38 (m, 6H), 7.18 (d, 1H), 7.1 (s, 1H), 6.58 (t, 1H), 3.75 (d, 2H), 3.47 (t, 2H), 2.42 (d, 2H), 1.76 (m, 2H); IR (drifts) $v_{max}$ 3374, 3180, 1681, 1520, 1498.

EXAMPLE 8

Synthesis of tetrahydro-4-[3-[4-(1H-benzoimidazol-1-yl)phenyl]thio]phenyl-2H-pyran-4-carboxamide Tetrahydro-4-[3-(4-fluorophenyl)thio]phenyl-2H-pyran-4-carboxamide (2.0 g, 6.02 mmole, 1 eq), dimethylsulfoxide (20 ml, 10 vol), benzoimidazole (1.43 g, 12.07 mmole, 2.0 eq) and cesium carbonate (3.93 g, 12.07 mmole, 2.0 eq) were added to a reaction flask set for boiling at reflux under a nitrogen atmosphere, and the reaction mixture was heated with stirring at 139–142° C. for 5 hours under nitrogen. After completion, the reaction was cooled (<30° C.) and quenched with water (20 ml, 10 vol). This resulted in formation of a precipitate. An exotherm of 10–15° C. was observed during the water addition. The reaction slurry so formed, was cooled to room temperature (15–25° C.) and then granulated for 1 h. The product was isolated by vacuum filtration and washed with water (20 ml, 10 vol) to obtain the crude product, which was dried overnight in a vacuum oven at 40° C. The crude product was dissolved in acetonitrile (130 ml) to form a solution which was filtered and then cooled to initiate crystallization, after a period of granulation at room temperature, product was isolated by filtration, washed with acetonitrile (36 ml) and dried to obtain a white solid (1.9 g, 74%): mp 166–168° C.; m/z430 (m+1); (Found C, 68.59; H, 5.27; N, 9.65; S, 7.64. $C_{25}H_{23}N_3O_2S$ requires C, 69.91; H, 5.40; N 9.78; S, 7.47.) $^1H$ NMR (300 MHz, DMSO) δ8.59 (s, 1H), 7.80 (d, 1H), 7.72 (d, 2H), 7.65 (d, 1H), 7.49–7.34 (m, 9H), 7.13 (s, 1H), 3.76 (d, 2H), 3.49 (t, 2H), 2.45 (d, 2H), 1.82 (m, 2H); IR (drifts) $V_{max}$ 3370, 3188, 1683, 1669, 1501.

EXAMPLE 9

Synthesis of tetrahydro-4-[3-[4-(4-methyl-1H-pyrazol-1-yl)phenyl]thio]phenyl-2H-pyran-4-carboxamide Tetrahydro-4-[3-(4-fluorophenyl)thio]phenyl-2H-pyran-4-carboxamide (2.0 g, 6.02 mmole, 1 eq), dimethylsulfoxide (20 ml, 10 vol), 4-methylpyrazole (0.991 g, 12.07 mmole, 2.0 eq) and cesium carbonate (3.93 g, 12.07 mmole, 2.0 eq) were added to a reaction flask set for boiling at reflux under a nitrogen atmosphere, and the reaction mixture was heated with stirring at 139–142° C. for 5 hours under nitrogen. After completion, the reaction was cooled (<30° C.) and quenched with water (20 ml, 10 vol). This resulted in formation of a precipitate. An exotherm of 10–15° C. was observed during the water addition. The reaction slurry so formed, was cooled to room temperature (15–25° C.) and then granulated for 1 h. The product was isolated by vacuum filtration and washed with water (20 ml, 10 vol) to obtain the crude product, which was dried overnight in a vacuum oven at 40° C. The crude product was dissolved in acetonitrile (70 ml) and propan-2-ol (115 ml) to form a solution which was filtered and then concentrated until the solution became cloudy, crystallization was established after a period of granulation in the temperature range 3–7° C., product was isolated by filtration, washed with cold propan-2-ol (20 ml) and dried to obtain a white solid (2.034 g, 86%): mp 202–204° C.; m/z 394 (m+1); (Found C, 66.99; H, 6.05; N, 10.47; S, 8.21. $C_{22}H_{23}N_3O_2S$ requires C, 67.15; H, 6.05; N, 10.47; S, 8.21.) $^1H$ NMR (300 MHz, DMSO) δ8.31 (s, 1H), 7.82 (d, 2H), 7.60 (s, 1H), 7.39 (m, 6H), 7.16 (dt, 1H), 7.10 (s, 1H), 3.73 (d, 2H), 3.46 (t, 2), 2.47 (d, 2H), 2.11 (s, 3H), 1.78 (m, 2H); IR (drifts) $v_{max}$ 3370, 3181, 1682, 1506.

EXAMPLE 10

Synthesis of tetrahydro-4-(3-bromophenyl)-2H-pyran-4-carboxamide

Propan-2-ol (100 ml), tetrahydro-4-(3-bromophenyl)-2H-pyran-4-nitrile (20.0 g, 0.075 mole, 1 eq.), potassium hydroxide (13.74 g, 0.245 mole, 3.26 eq.) were added to a

41 reaction flask set for boiling at reflux under a nitrogen atmosphere, and the reaction mixture was heated with stirring at reflux, about 82° C. for 5–6 hours under nitrogen. After reaction completion, the mixture was cooled (<30° C.) and quenched with water (100 ml). The resultant slurry was filtered and the product residue, washed with water (30 ml), and dried under vacuum at 45–50° C. to yield a white solid. Yield 19.05 g, 89.2%. mp 245–247° C.; m/z 285 (m+1); $^1$H NMR (300 MHz, DMSO) δ7.43 (m, 5H), 7.14 (s, 1H), 3.76 (d, 2H), 3.47 (t, 2H), 2.44 (d, 2H), 1.79 (m, 2H).; IR (drifts) $v_{max}$ 3363, 3174, 3062, 2973, 2935, 2879, 2828, 1685, 1631, 1588.

EXAMPLE 11

Synthesis of tetrahydro-4-[3-(4-fluorophenyl)thio]phenyl-2H-pyran-4-carboxamide

Butan-1-ol (8 ml), tetrahydro-4-(3-bromophenyly2H-pyran-4-carboxamide (2.97 g, 10.45 mmole, 1 eq.), potassium tert-butoxide (2.34 g, 20.9 mmole, 2 eq.), water (4 ml, 0.39 mole, 2 eq.), tetrakis(triphenylphosphine)palladium(0) (0.242 g, 0.209 mmole, 0.02 eq.) and 4-fluorothiophenol (1.34 g, 10.45 mmole, 1 eq.) were added to a reaction flask set for boiling at reflux under a nitrogen atmosphere. The resultant reaction mixture was heated at approximately 100° C. for 8–10 h to drive it to completion. The reaction mixture was cooled to ambient temperature, 20–25° C. and butan-1 ol (10 ml) was added to obtain a slurry. The crude product was isolated by filtration and washed with butan-1-ol (3 ml) and sucked dry. Crude dry product was stirred in methanol (15 ml), the resultant slurry was filtered and the product cake washed with methanol (5 ml) and dried under vacuum at 40–45° C. The partially purified product was heated to reflux in prop-an-2-ol (45 ml) for 30 minutes, cooled and the resultant slurry filtered and the product cake washed with propan-2-ol (5 ml) and dried under vacuum at 40–45° C. The solid obtained (3.22 g) was further purified by stirring in tetrahydrofuran (240 ml) at 20–25° C. An insoluble solid impurity was removed by filtration, and the product containing filtrate was concentrated to 20 ml and treated with heptane (20 ml). The resultant product slurry was filtered, the product filter cake washed with heptane (8 ml) and dried under vacuum at 40–45° C. Yield 1.62 g (46.8%): mp 175–178° C.; m/z 332 (m+1); spectral data as in Example 2.

What is claimed is:

1. A process for preparing a substantially pure mesylate salt of Formula (1.0.1):

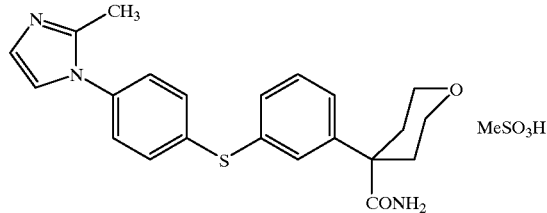

comprising:
(a) preparing a compound of Formula (2.0.0):

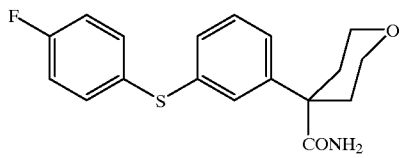

comprising:
(1) establishing a reaction mixture consisting of
(i) tetrahydro-4-(3-bromo-phenyl)-2H-pyran-4-nitrile of Formula (3.2.0):

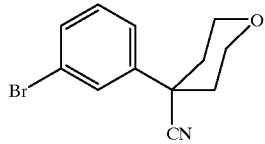

and
(ii) 4-fluorothiophenol of Formula (4.0.0):

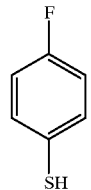

(iii) in a solvent selected from the group consisting of iso-propyl alcohol, sec-butyl alcohol, iso-pentyl alcohol, and 2-heptanol, optionally as an aqueous mixture thereof;
(iv) in the presence of a strong base selected from the group consisting of sodium hydroxide, NaOH; and potassium hydroxide, KOH;
and further
(v) in the presence of a transition metal catalyst comprising a member independently selected from the group consisting of palladium metal complexes;
followed by
(2) heating said reaction mixture; whereby there is produced said compound of Formula (2.0.0);
(b) establishing a reaction mixture consisting of said compound of Formula (2.0.0) and a compound of Formula (1.3.10):

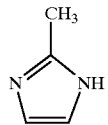

(1) in an aprotic solvent;
(2) in the presence of cesium carbonate, $CS_2CO_3$;
followed by
(c) heating said reaction mixture at reflux, under a nitrogen atmosphere; whereby there is produced a compound of Formula (1.0.0):

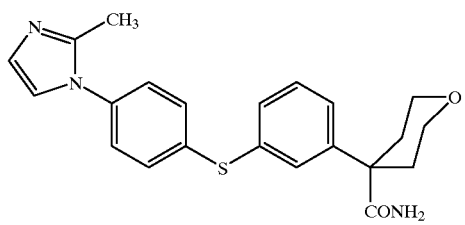

followed by (d) forming a concentrated methanol solution of said compound of Formula (1.0.0) to which there is then added methanesulfonic acid, MeSO$_3$H; followed by further concentration and the addition of ethyl acetate ad seriatim until a crystalline product is isolated comprising substantially pure mesylate salt of Formula (1.0.1)

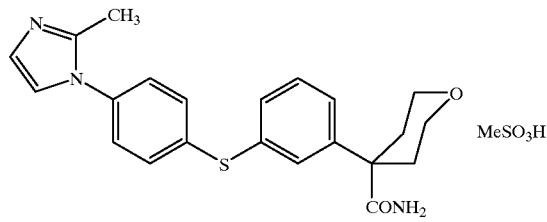

or, alternatively, followed by (e) forming a concentrated methanol solution of said compound of Formula (1.0.0) to which there is then added methanesulfonic acid, MeSO$_3$H; followed by filtering of the mixture, preferably through activated carbon, after which there follows further concentration and the addition of ethyl acetate ad seriatim until a crystalline product is isolated comprising said substantially pure mesylate salt of Formula (1.0.1).

2. A process according to claim 1 wherein said palladium metal complex is a member selected from the group consisting of:

tetrakis(triphenylphosphine)palladium(0), [(C$_6$H$_5$)$_3$P]$_4$Pd(0);

tetrakis(methyldiphenylphosphine)palladium(0), [(C$_6$H$_5$)$_2$PCH$_3$]$_4$Pd(0);

trans-dichlorobis(methyldiphenylphosphine)palladium(II), [(C$_6$H$_5$)$_2$PCH$_3$]$_2$PdCl$_2$;

dichlorobis[methylenebis(diphenylphosphine)]dipalladium-dichloromethane adduct;

dichlorobis(triphenylphosphine)palladium(II), [(C$_6$H$_5$)$_3$P]$_2$PdCl$_2$;

tris(dibenzylideneacetone)dipalladium(0)-chloroform adduct, (C$_6$H$_5$CH=CHCOCH=CHC$_6$H$_5$)$_3$Pd$_2$·CHCl$_3$;

bis(dibenzylideneacetone)palladium(0), (C$_6$H$_5$CH=CHCOCH=CHC$_6$H$_5$)$_2$Pd;

[1,1'-bis(diphenylphosphino)ferrocene]dichloropalladium(II), complex with dichloromethane bis[1,2-bis(diphenylphosphino)ethane]palladium(II); and (π-allyl)palladium(II) chloride dimer.

* * * * *